US011403790B2

(12) United States Patent
Suzuki et al.

(10) Patent No.: US 11,403,790 B2
(45) Date of Patent: Aug. 2, 2022

(54) X-RAY CT APPARATUS AND SCAN PLANNING APPARATUS

(71) Applicant: Canon Medical Systems Corporation, Otawara (JP)

(72) Inventors: Yojiro Suzuki, Vernon Hills, IL (US); Takahiro Yoda, Nasushiobara (JP); Risa Onishi, Otawara (JP); Junki Hashizume, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 330 days.

(21) Appl. No.: 15/935,373

(22) Filed: Mar. 26, 2018

(65) Prior Publication Data

US 2018/0276854 A1  Sep. 27, 2018

(30) Foreign Application Priority Data

Mar. 27, 2017  (JP) .............................. JP2017-061289
Mar. 23, 2018  (JP) .............................. JP2018-055799

(51) Int. Cl.
*G06T 11/00* (2006.01)
*A61B 6/03* (2006.01)
(Continued)

(52) U.S. Cl.
CPC ............ *G06T 11/005* (2013.01); *A61B 5/318* (2021.01); *A61B 6/027* (2013.01); *A61B 6/032* (2013.01);
(Continued)

(58) Field of Classification Search
CPC ... G06T 11/005; G06T 2210/41; A61B 6/503; A61B 5/0402; A61B 6/032; A61B 6/027;
(Continued)

(56) References Cited

U.S. PATENT DOCUMENTS

2007/0140535 A1\* 6/2007 Li .......................... A61B 6/463
                                                              382/128
2009/0161822 A1\* 6/2009 Hagiwara ............ A61B 6/0487
                                                               378/20
(Continued)

FOREIGN PATENT DOCUMENTS

JP    2000-051208    2/2000
JP    2007-275551   10/2007
(Continued)

OTHER PUBLICATIONS

Japanese Office Action dated Nov. 30, 2021, issued in Japanese Patent Application No. 2018-055799.

*Primary Examiner* — Ashley K Buran
*Assistant Examiner* — Kaitlyn E Sebastian
(74) *Attorney, Agent, or Firm* — Oblon, McClelland, Maier & Neustadt, L.L.P.

(57) ABSTRACT

According to one embodiment, an X-ray CT apparatus is adapted to perform helical scanning on a subject placed on a couch top and perform reconstruction processing based on acquired projection data. The X-ray CT apparatus sets a first imaging range within an imaging range for the helical scanning, sets at least one of a start range and an end range in the first imaging range as a boundary range, sets a first view number for use in the reconstruction processing for a non-boundary range other than the boundary range in the first imaging range, and sets a view number for use in the reconstruction processing for the boundary range to be smaller than the first view number.

8 Claims, 14 Drawing Sheets

(51) Int. Cl.
*A61B 6/00* (2006.01)
*A61B 6/02* (2006.01)
*G01N 23/046* (2018.01)
*A61B 5/318* (2021.01)

(52) U.S. Cl.
CPC .............. *A61B 6/503* (2013.01); *A61B 6/541* (2013.01); *G01N 23/046* (2013.01); *G06T 2210/41* (2013.01)

(58) Field of Classification Search
CPC ...... A61B 6/541; G01N 23/046; G03B 42/02; H05G 1/00
See application file for complete search history.

(56) References Cited

U.S. PATENT DOCUMENTS

| | | | | |
|---|---|---|---|---|
| 2010/0172563 | A1* | 7/2010 | Hagiwara | ............ G06T 11/006 |
| | | | | 382/131 |
| 2012/0039432 | A1* | 2/2012 | Kondo | ................... A61B 6/482 |
| | | | | 378/4 |

FOREIGN PATENT DOCUMENTS

| | | | |
|---|---|---|---|
| JP | 2007275551 A | * | 10/2007 |
| JP | 2009-082306 | | 4/2009 |
| JP | 2009-095510 | | 5/2009 |
| JP | 2009-148469 A | | 7/2009 |

* cited by examiner

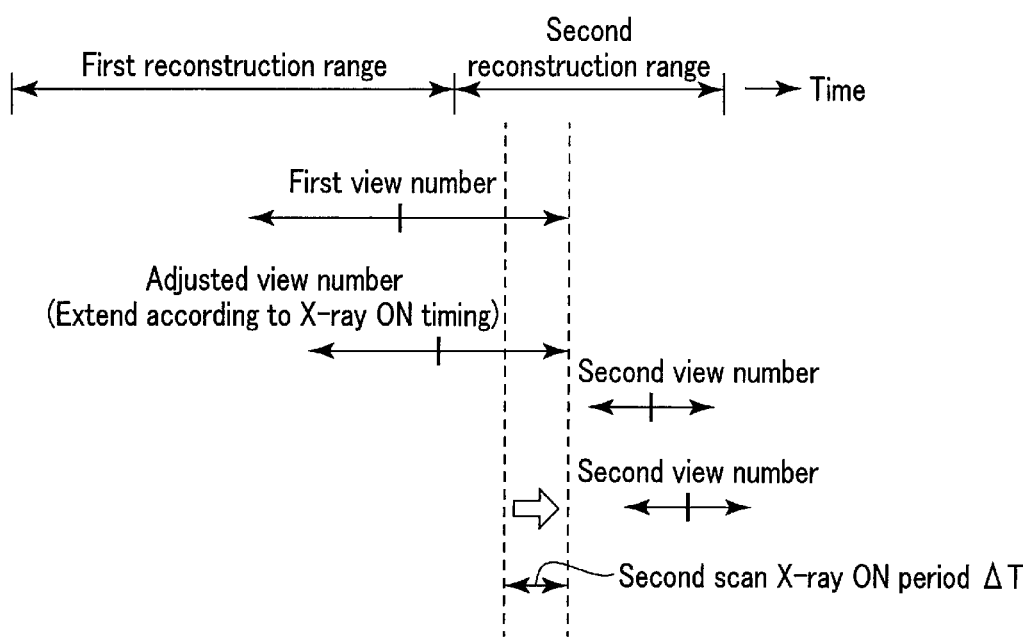
F I G. 9

X-RAY CT APPARATUS AND SCAN PLANNING APPARATUS

CROSS-REFERENCE TO RELATED APPLICATIONS

This application is based upon and claims the benefit of priority from prior Japanese Patent Applications No. 2017-61289, filed on Mar. 27, 2017, and No. 2018-55799, filed on Mar. 23, 2018, the entire contents of all of which are incorporated herein by reference.

FIELD

Embodiments described herein relate generally to an X-ray computed tomography (CT) apparatus and a scan planning apparatus.

BACKGROUND

An X-ray CT apparatus is a type of medical image diagnostic apparatus that creates images of internal sites of a subject by scanning the subject with X-rays and processing the acquired data using a computer.

Some X-ray CT apparatuses are furnished with an electrocardiogram (ECG)-gated scanning function. The ECG-gated scanning periodically acquires projection data through, for example, intermittent radiations based on cycles of electrocardiographic waveforms. This data acquisition is repeated so that projection data is acquired each time the same cardiac time phase is reached, in order to complete a set of projection data covering different projecting directions, for example, as much as 360°, for a given cardiac time phase. Use of such a projection data set allows for the reconstruction of tomograms that do not involve an artifact from heartbeats. The ECG-gated scanning is a scanning technique used when, for example, observing the flow of a contrast medium injected into a subject.

Also, variable helical pitch (VHP) scanning is known as a technique adopted in X-ray CT apparatuses for scanning a subject. The VHP scanning is helical scanning, i.e., continuous scanning performed along the longitudinal direction of a couch carrying a subject with an X-ray tube for X-ray generation and an X-ray detector helically rotating around the couch (couch top). The VHP scanning is capable of scanning while modulating the scan pitch of the helical scanning. The scan pitch here equals the distance traveled by the couch for the period of one-rotation scanning. Also, modulating basically indicates changing the scan pitch according to, for example, a traveling speed of the couch carrying a subject. The modulation is however not limited to this, but may also indicate changing the scan pitch according to the rotational speed of the X-ray tube and the X-ray detector.

During this VHP scanning, the ECG-gated scanning may also be performed. The VHP scanning and the ECG-gated scanning are different from each other in number of projection data used for the reconstruction of one CT image, that is, different in number of views. More specifically, the ECG-gated scanning is expected to take still images of a heart; thus, it uses a smaller number of views for reconstruction (e.g., a view number that is half the number of data acquisition operations performed for a period of one rotation of an X-ray tube and an X-ray detector) in order to have a fast temporal resolution. On the other hand, the VHP scanning is expected to utilize all the scanned views; thus, it uses a greater number of views than the ECG-gated scanning for CT-image reconstruction. In this context, focusing on a boundary between a first scan and a second scan with the assumption that the first scan is the VHP scanning performed for the period other than the ECG-gated scanning period and the second scan is the ECG-gated scanning among the VHP scanning, the first scan involves a greater number of views than the second scan.

Owing to this, the scan area of the first scan can run off the imaging range (reconstruction range) intended for the first scan and overlap with the scan area of the second scan, resulting in the area which should not be required for the image reconstruction with the ECG-gated scanning being exposed to the X-ray radiations of the first scan. As such, the process cannot proceed to the intermittent radiations of the second scan until the first scan is finished, forcing the time up to the initial turning off of the X-rays in the second scan to be prolonged.

The same situation is inherent in the instances where a process does not include the second scan but only the first scan to perform normal helical scanning. In these instances, too, the scan area would run off the imaging range for the first scan, and the outside area would accordingly be irradiated with X-rays as discussed above.

The objects intended by the embodiments include reducing X-ray radiations to areas deviated from the imaging range for helical scanning.

BRIEF DESCRIPTION OF THE DRAWINGS

FIG. 9 is a schematic diagram showing a relationship between view numbers when a first scan and a second scan according to a second embodiment are combined.

DETAILED DESCRIPTION

In general, according to one embodiment, an X-ray CT apparatus is adapted to perform helical scanning on a subject placed on a couch top and perform reconstruction processing based on acquired projection data. The X-ray CT apparatus includes an X-ray generator, an X-ray detector, and processing circuitry.

The X-ray generator is configured to generate an X-ray for emission to the subject.

The X-ray detector is configured to detect the X-ray via the subject to acquire the projection data.

The processing circuitry is configured to set a first imaging range within an imaging range for the helical scanning.

The processing circuitry is configured to set at least one of a start range and an end range in the first imaging range as a boundary range.

The processing circuitry is configured to set a first view number for use in the reconstruction processing for a non-boundary range other than the boundary range in the first imaging range.

The processing circuitry is configured to set a view number for use in the reconstruction processing for the boundary range to be smaller than the first view number.

The embodiments of an X-ray CT apparatus and a scan planning apparatus will be described with reference to the drawings. There are various types of X-ray CT apparatuses, such as a rotate/rotate type (third-generation CT) allowing an X-ray tube and a detector to integrally rotate around a subject, and a stationary/rotate type (fourth-generation CT) including many X-ray detecting elements fixed and arrayed in a ring pattern and allowing only an X-ray tube to rotate around a subject. The embodiments are applicable to both types. For the sake of description, the third-generation CT will be taken as an example.

First Embodiment

Figure 1:
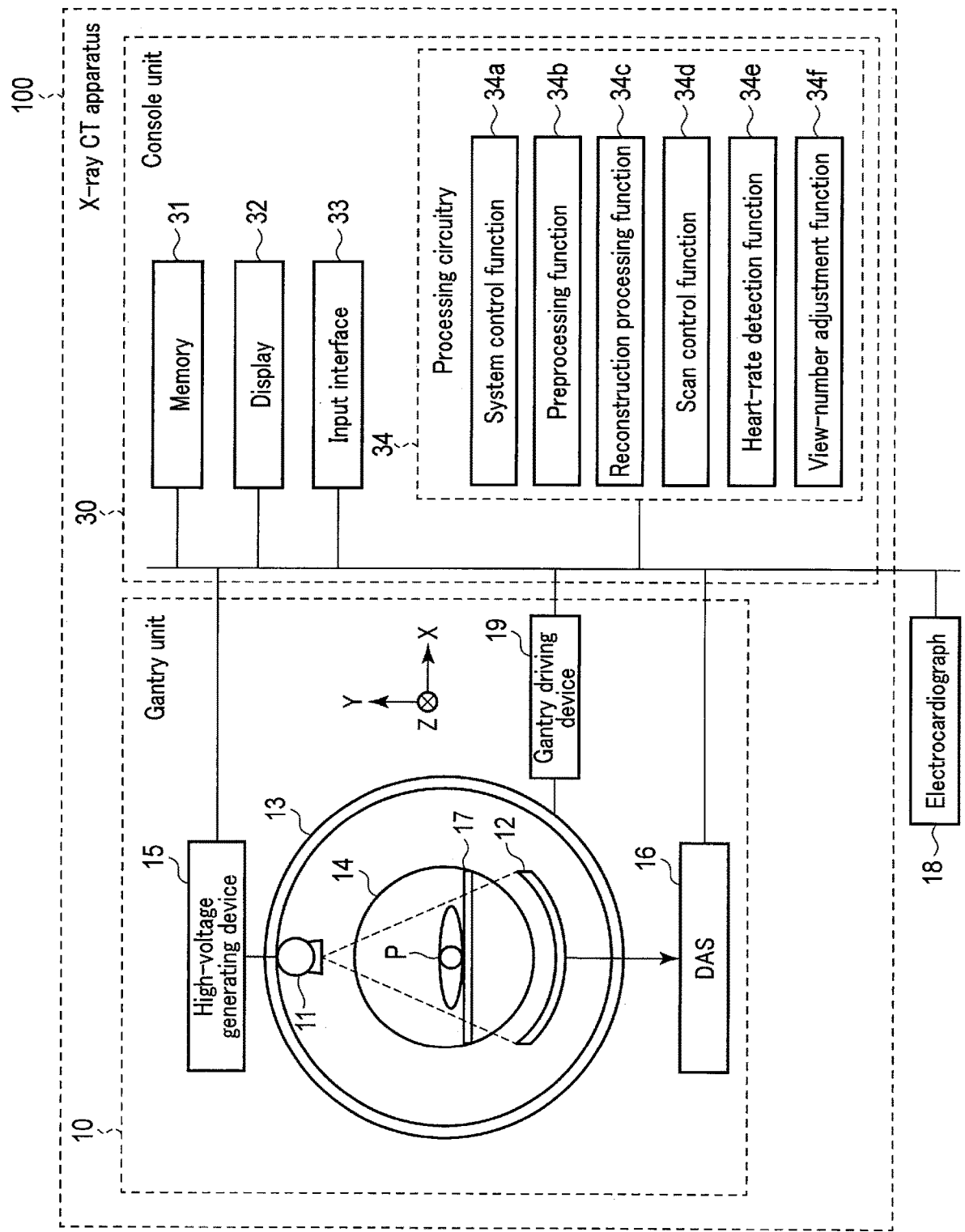
FIG. 1 is a block diagram showing an overview configuration of an X-ray CT apparatus according to a first embodiment.

First, a configuration of an X-ray CT apparatus 100 according to the first embodiment will be described using FIGS. 1 to 7. FIG. 1 is a block diagram showing an overview configuration of the X-ray CT apparatus 100 according to the first embodiment. The X-ray CT apparatus 100 of FIG. 1 includes a gantry unit 10 and a console unit 30.

[Gantry unit] The gantry unit 10 is a unit to emit X-rays to a subject P and to acquire detection data for the X-rays that have passed through the subject. The gantry unit 10 includes an X-ray generating device 11, an X-ray detector 12, a rotation frame 13, a high-voltage generating device 15, a data acquisition system (DAS) 16, and a gantry driving device 19. The gantry unit 10 is one example of a gantry.

The X-ray generating device 11 includes an X-ray tube for generating X-rays (e.g., a conical or pyramid-shape vacuum tube for generating X-ray beams). The X-ray tube is a vacuum tube that generates X-rays by thermionic emission from a cathode (filament) to an anode (target) using a high-voltage application from the high-voltage generating device 15. The X-rays generated at the X-ray generating device 11 are emitted toward the subject P placed on a couch top 17. The X-ray generating device 11 according to this embodiment performs ON/OFF switching of the X-rays based on electrocardiographic waveforms of the subject P during the ECG-gated scanning, under the control of a scan control function 34d described later. The X-ray generating device 11 is one example of an X-ray generator.

The X-ray detector 12 includes multiple rows of X-ray detecting elements, each arranging a plurality of X-ray detecting elements in the channel direction along a single arc that has a center on the focal point of the X-ray tube. The X-ray detector 12 detects X-rays having passed through the subject P and outputs an electrical signal corresponding to the dose of the X-rays to the DAS 16. As the X-ray detector 12, for example, an X-ray detector (area detector) including a plurality of X-ray detecting elements arranged in each of two mutually-orthogonal directions (slice direction and channel direction) is employed. As the multiple rows of X-ray detecting elements, there are, for example, 320 rows provided along the slice direction. The slice direction represents a direction of the rotational axis of the rotation frame 13, and the channel direction represents a direction of the rotation of the X-ray generating device 11. This embodiment assumes that the rotational-axis direction of the non-tilted state rotation frame 13 or the longitudinal direction of the couch top 17 is defined as a Z-axis direction, an axial direction that is orthogonal to the Z-axis direction and horizontal to the floor face is defined as an X-axis direction, and an axial direction that is orthogonal to the Z-axis direction and vertical to the floor face is defined as a Y-axial direction.

Also, the X-ray detector 12 is, for example, an indirect conversion-type detector including a grid, a scintillator array, and an optical sensor array.

The scintillator array includes a plurality of scintillators with scintillator crystals that output light of a photon quantity corresponding to an incident X-ray dose.

The grid is provided on the X-ray incident-side face of the scintillator array, and includes an X-ray shielding plate that has a function of absorbing scattered X-rays. The grid may be called a collimator (one-dimensional collimator or two-dimensional collimator).

The optical sensor array has a converting function to produce electrical signals according to the light amount from the scintillators, and includes, for example, an optical sensor such as a photomultiplier tube (PMT).

Note that the X-ray detector 12 may also be a direct conversion-type detector that includes semiconductor elements for converting incident X-rays into electrical signals. The X-ray detector 12 and the DAS 16 constitute one example of an X-ray detector.

The rotation frame 13 is a circular frame that supports the X-ray generating device 11 and the X-ray detector 12 so that they face each other with the subject P therebetween. The rotation frame 13, while supporting the X-ray generating device 11 and the X-ray detector 12, allows them to rotate about the subject P during the scanning of the subject P. The rotation frame 13 includes a bore 14 penetrating in the slice direction. The rotation frame 13 further carries and supports the high-voltage generating device 15 and the DAS 16, in addition to the X-ray generating device 11 and the X-ray detector 12. Detection data prepared by the DAS 16 is transmitted via optical communication from a transmitter including a light-emitting diode (LED) at the rotation frame 13 to a receiver including a photodiode at the non-rotating portion of the gantry unit 10 (e.g., a stationary frame, which is omitted in FIG. 1), and transferred to the console unit 30.

Note that the manner for transmitting the detection data from the rotation frame 13 to the non-rotating portion of the gantry unit 10 is not limited to such optical communication, but any technique may be adopted as long as it permits contactless data transmission. The rotation frame 13 is one example of a rotator.

The high-voltage generating device 15 is voltage generating circuitry that applies a high voltage to the X-ray generating device 11 (the following descriptions will assume "voltage" to be a voltage between the anode and the cathode in the X-ray tube). The X-ray generating device 11 generates X-rays using the high voltage from the high-voltage generating device 15. The high-voltage generating device 15 is one example of a high-voltage generator.

The DAS 16 is electric circuitry that acquires detection data by collecting electrical signals (receives data) from the respective X-ray detecting elements of the X-ray detector 12. More specifically, the DAS 16 includes an amplifier for performing amplification processing on the electrical signals output from each X-ray detecting element and an A/D converter for converting the electrical signals into digital signals, so that the DAS 16 generates detection data corresponding to each direction of the X-ray emission from the X-ray tube. The X-ray emission direction may be called a view. The DAS 16 then outputs the generated detection data for each view to processing circuitry 34 of the console unit 30. For example, the DAS 16 outputs to the processing circuitry 34 of the console unit 30 the data in which detection data indicative of the detected X-ray amount in each X-ray detecting element is mapped for each X-ray emission direction (sinogram data). The number of detection data for each view included in this one sinogram data will be called a view number. In this embodiment, the DAS 16 outputs sinogram data of different view numbers in the first scan and the second scan described later. The first scan is a scanning operation performed for the period other than an ECG-gated scanning period among VHP scanning. The second scan is ECG-gated scanning among the VHP scanning. Also, the DAS 16 is one example of a data acquirer.

The gantry driving device 19 has a function of rotating the rotation frame 13 and driving the couch and the couch top 17, and includes, for example, a motor or an actuator. The gantry driving device 19 according to this embodiment moves the couch along the rotational-axis direction of the rotation frame 13 during the first scan and the second scan, under the control of the scan control function 34d described later. Note that the control is performed so that the gantry driving device 19 moves the couch top 17 slower in the second scan than in the first scan. The rotational-axis direction of the rotation frame 13 may be called a longitudinal direction of the couch top 17 or a body-axis direction of the subject P. The method for moving the couch top 17 may include an option of moving only the couch top 17 or an option of moving the couch top 17's supporting frame (not shown) together. Also, the method for changing the relative positional relationship between the couch top 17 and the gantry unit 10 during the helical scanning may include an option of moving the couch top 17 or an option of moving the gantry unit 10, or a combination of such. By way of example, descriptions of each embodiment will be given assuming that the option of moving the couch top 17 is adopted. The gantry driving device 19 is one example of a driver.

[Console Unit]

The console unit 30 is a unit used for operational inputs to the X-ray CT apparatus 100. The console unit 30 is furnished with various functions including reconstruction of CT image data indicative of the internal conditions of the subject P (tomogram data, volume data, etc.) from the sinogram data acquired by the DAS 16 of the gantry unit 10. The console unit 30 includes a memory 31, a display 32, an input interface 33, and processing circuitry 34. Note that the console unit 30 will be described as a unit separate from the gantry unit 10, but it may be incorporated into the gantry unit 10 or its components may be partially included in the gantry unit 10. Also, the console unit 30 may adopt a configuration to execute multiple functions through a single console, or may adopt a configuration to execute multiple functions through discrete consoles. For example, functions of the processing circuitry 34, such as a preprocessing function 34b and a reconstruction processing function 34c, may be separately provided. The console unit 30 is one example of a console.

Figure 4:
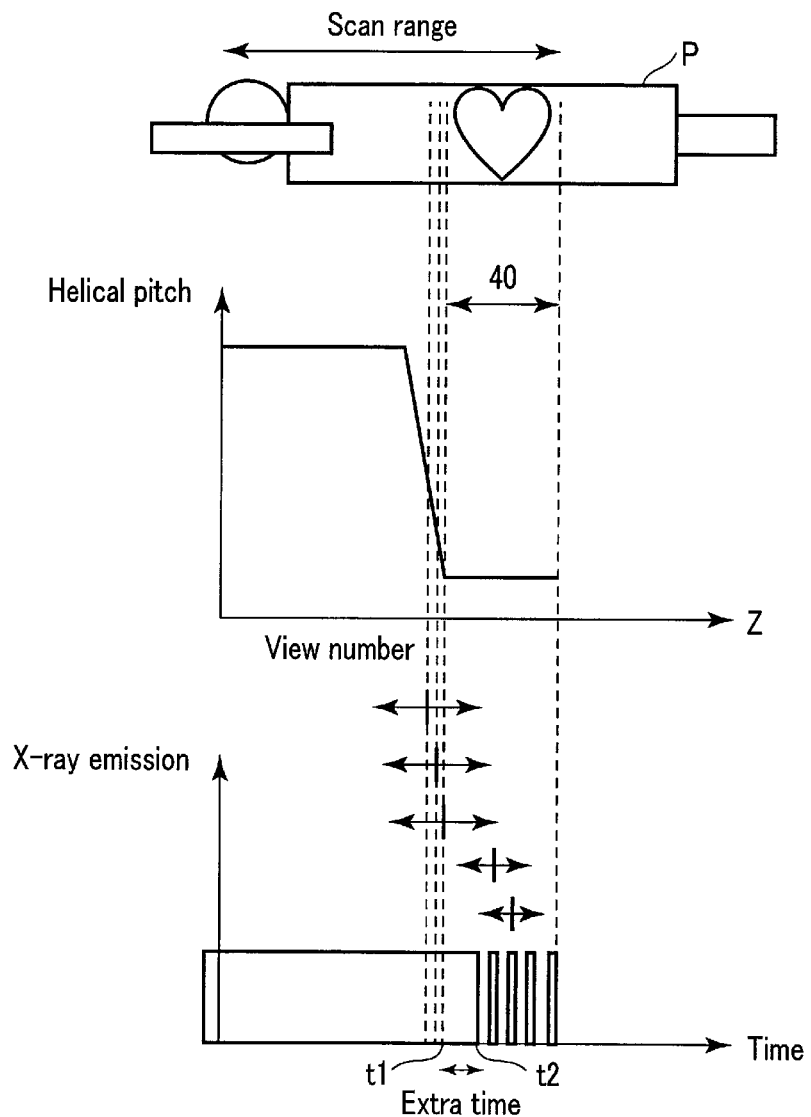
FIG. 4 is a schematic diagram showing an overview of a helical pitch, a view number, and X-ray radiation timing in a first scan and a second scan according to a comparative example of the embodiments.
Figure 5:
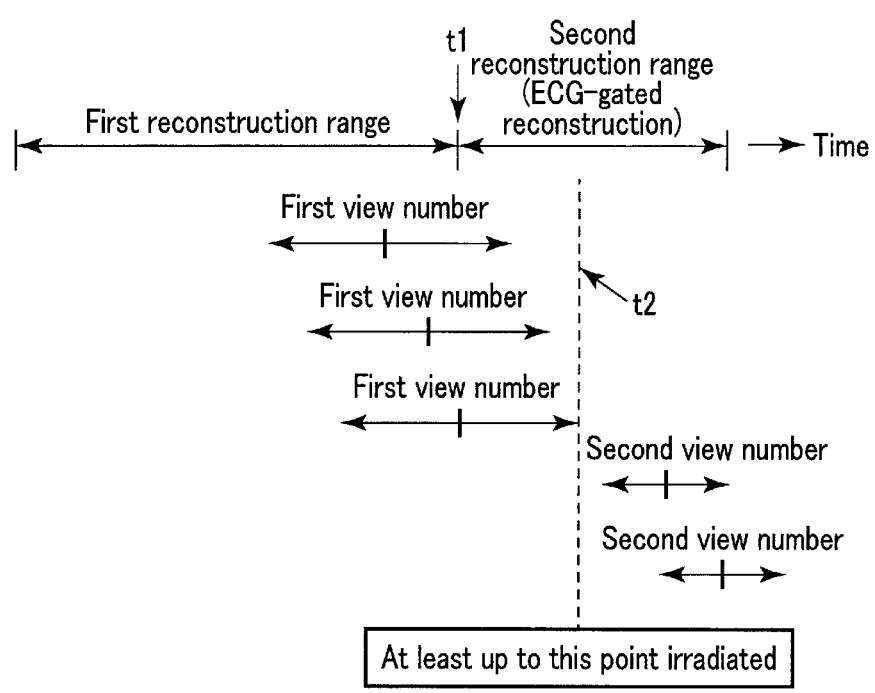
FIG. 5 is a schematic diagram showing a relationship between view numbers when the first scan and the second scan are combined according to the comparative example.

The memory 31 is realized by, for example, a semiconductor memory device such as a random access memory (RAM), a read only memory (ROM), or a flash memory, or a hard disk, an optical disk, etc. The memory 31 stores detection data, projection data as the detection data having undergone the later-described preprocessing, or CT image data after reconstruction processing, and so on. Projection data, reconstructed image data, etc., may be stored not only by the memory 31 but also by cloud servers that can be connected to the X-ray CT apparatus 100 via a communication network such as the Internet. For example, a cloud server may store projection data, reconstructed image data, etc., upon receipt of a save request from the X-ray CT apparatus 100. Also, the memory 31 according to this embodiment stores a subject P's electrocardiographic waveform output from an electrocardiograph 18 (described later), imaging ranges corresponding to the respective reconstruction ranges of the first and second scans, boundary ranges, view numbers, helical pitches, field of view (FOV), and so on, as shown in FIGS. 2 to 7. Note, however, that the first view numbers for the boundary ranges shown in FIGS. 4 and 5 are view numbers used in a comparative example and not used in the present embodiment, while they are settable. Detailed descriptions with reference to FIGS. 2 to 7 will be given later. The memory 31 is one example of a storage.

The display 32 displays various types of information. For example, the display 32 outputs medical images (CT images) generated by the processing circuitry 34, graphical user interfaces (GUIs) to accept various operations from operators, and so on. For example, the display 32 is a liquid crystal display (LCD) or a cathode ray tube (CRT) display. For example, the display 32 displays CT images obtained by the first and second scans and subjected to reconstruction processing. Also, the display may be called a display device. The display 32 is one example of a display. The display 32 may be provided at the gantry unit 10. The display 32 may be a desktop type, or constituted as a tablet terminal capable of wireless communication with the main part of the console unit 30.

The input interface 33 accepts various input operations from operators, converts the accepted input operations into electrical signals, and outputs them to the processing circuitry 34. For example, the input interface 33 accepts acquisition conditions to apply when acquiring projection data, reconstruction conditions to apply when reconstructing CT images, image-processing conditions to apply when generating processed images from CT images, and so on, from an operator. The input interface 33 also accepts, for example, settings for imaging ranges corresponding to the respective reconstruction ranges of the first and second scans, boundary ranges, view numbers, helical pitches, and FOV, as shown in FIGS. 3 to 7, from an operator. Note that the first view numbers for the boundary range shown in FIGS. 4 and 5 are view numbers used in a comparative example and not used in the present embodiment, while they are also settable. Also, this input interface 33 is realized by, for example, a mouse, a keyboard, a trackball, switches, buttons, a joystick, etc. The input interface 33 can adopt a GUI for its portion. The input interface 33 is one example of an inputter. The input interface 33 may be provided at the gantry unit 10. The input interface 33 may be implemented using a tablet terminal, etc. capable of wireless communication with the main part of the console unit 30.

The processing circuitry 34 controls operations of the entire X-ray CT apparatus 100. For example, the processing circuitry 34 performs various types of processing on the detection data transmitted from the DAS 16. The processing circuitry 34 includes a system control function 34a, the preprocessing function 34b, the reconstruction processing function 34c, the scan control function 34d, and a heart-rate detection function 34e. The processing circuitry 34 is one example of a processor.

The system control function 34a controls each function of the processing circuitry 34 based on the input operations accepted from operators via the input interface 33.

The system control function 34a also sets scan plans including imaging ranges, boundary ranges, and view numbers, according to the operations on the input interface 33. For example, the system control function 34a sets a first imaging range within the imaging range for the helical scanning, sets at least one of a start range and an end range in the first imaging range as a boundary range, sets a first view number for use in the reconstruction processing for a non-boundary range other than the boundary range in the first imaging range, and sets a view number for use in the reconstruction processing for the boundary range to be smaller than the first view number. In this instance, the boundary range may be set by, for example, designating an end range having a predetermined length to be the boundary range. The value of the "predetermined length" may be set in the form of, for example, a presetting in a parameter file in the memory 31. The system control function 34a may set the view number for use in the reconstruction processing for the boundary range so that it becomes small at once as shown in, for example, FIG. 6. The system control function 34a may also set the view number for use in the reconstruction processing for the boundary range so that it decreases in a stepwise manner as shown in, for example, FIG. 7. As the technique for the stepwise decrease, a number of optional techniques are available as appropriate, such as a technique to uniformly decrease the view number, and a technique to abruptly decrease the view number near the end portion. Also, the term "stepwise" covers both the "continuous" and "discrete" meaning, as narrow steps would constitute a "continuous" nature and wide steps would constitute a "discrete" nature.

The system control function 34a may also set a second imaging range adjacent to the boundary range on the side opposite to the non-boundary range, set a second view number for use in the reconstruction processing for the second imaging range to be smaller than the first view number, and set a minimum view number for use in the reconstruction processing for the boundary range to be equal to the second view number. As the second view number, any value can be adopted as long as it is smaller than the first view number and equal to or greater than the view number under a half-scan reconstruction mode. In this instance, the system control function 34a may set the view number for use in the reconstruction processing for the boundary range so that it becomes small at once or decreases in a stepwise manner as discussed above. If the view number for use in the reconstruction processing for the boundary range is set to become small at once, this view number may be set at the same value as the second view number.

The system control function 34a may set a scan condition so that a first helical pitch is used for the non-boundary range, a second helical pitch that is narrower than the first helical pitch is used for the second imaging range, and a helical pitch modulated between the first helical pitch and the second helical pitch is used for the boundary range. This scan condition is included in the scan plan. The scan condition may be referred to by the later-described scan control function 34d to control the gantry driving device 19.

The system control function 34a takes total control of the X-ray CT apparatus 100 by controlling the operations of the gantry unit 10, the console unit 30, and a couch unit (not shown). The system control function 34a is one example of a system controller. Also, in the system control function 34a, the function of setting the scan plan is one example of a setter. The system controller may or may not include the setter.

The preprocessing function 34b performs preprocessing such as logarithmic conversion, offset correction, sensitivity correction, and beam hardening correction, on the detection data output from the DAS 16 or the sinogram data generated from the detection data, and produces projection data. Note that data before the preprocessing (detection data, sinogram data) and data after the preprocessing may be generically called projection data. The preprocessing function 34b is one example of a preprocessor.

The reconstruction processing function 34c performs reconstruction processing on the projection data produced by the preprocessing function 34b to generate CT image data (tomogram data, volume data, etc.). To reconstruct a CT image, a full-scan reconstruction mode requires projection data covering one circumference of the subject P, i.e., data of a 360° projection. A half-scan reconstruction mode also requires projection data as much as an amount of 180° plus a fan angle. Both the reconstruction modes are applicable to the present embodiment. For example, it is possible to use the first view number as a view number under the full-scan reconstruction mode, and use the second view number as a view number under the half-scan reconstruction mode. Tomogram data means image data of a subject P's specific tomographic plane, and volume data means subject P's three-dimensional image data constructed by a collection of tomogram data. Reconstruction of the tomogram data may adopt any technique, such as two-dimensional Fourier transform, convolution back-projection, and iterative approximation reconstruction. The volume data is produced through the interpolation processing on a collection of reconstructed tomogram data. Reconstruction of the volume data may adopt any technique, such as cone-beam reconstruction, multi-slice reconstruction, and magnification reconstruction. The reconstruction processing function 34c is one example of a reconstruction processor.

The scan control function 34d controls various operations for X-ray scanning. For example, the scan control function 34d controls the high-voltage generating device 15 to apply a high voltage to the X-ray generating device 11 to generate X-rays. Also, the scan control function 34d controls the rotation frame 13 to rotate during scanning. In this embodiment, the scan control function 34d controls the gantry driving device 19 to move the couth top 17 slower in the second scan than in the first scan. The scan control function 34d also acquires subject P's electrocardiographic waveform data from the later-described heart-rate detection function 34e and controls ON/OFF timing of the X-rays in the second scan. The scan control function 34d is one example of a scan controller.

The heart-rate detection function 34e is a function to identify, for example, a cycle of later-described P-waves from the electrocardiographic waveform data obtained by the external electrocardiograph 18 connected to the X-ray CT apparatus 100, and to measure the heart rate of the subject P based on this cycle. The heart-rate detection function 34e outputs the electrocardiographic waveform data obtained from the electrocardiograph 18 to the scan control function 34d. The heart-rate detection function 34e is one example of a detector.

The electrocardiograph 18 is a sensor provided independently of the X-ray CT apparatus 100 and detects weak currents caused by the heartbeat of the subject P. The electrocardiograph 18 outputs temporal changes of the detected currents as an electrocardiogram. Using the electrocardiographic waveforms expressed in this electrocardiogram, the scan control function 34d of the processing circuitry 34, as described later, controls the X-ray emission of the X-ray generating device 11 (ECG-gating function).

Figure 2:
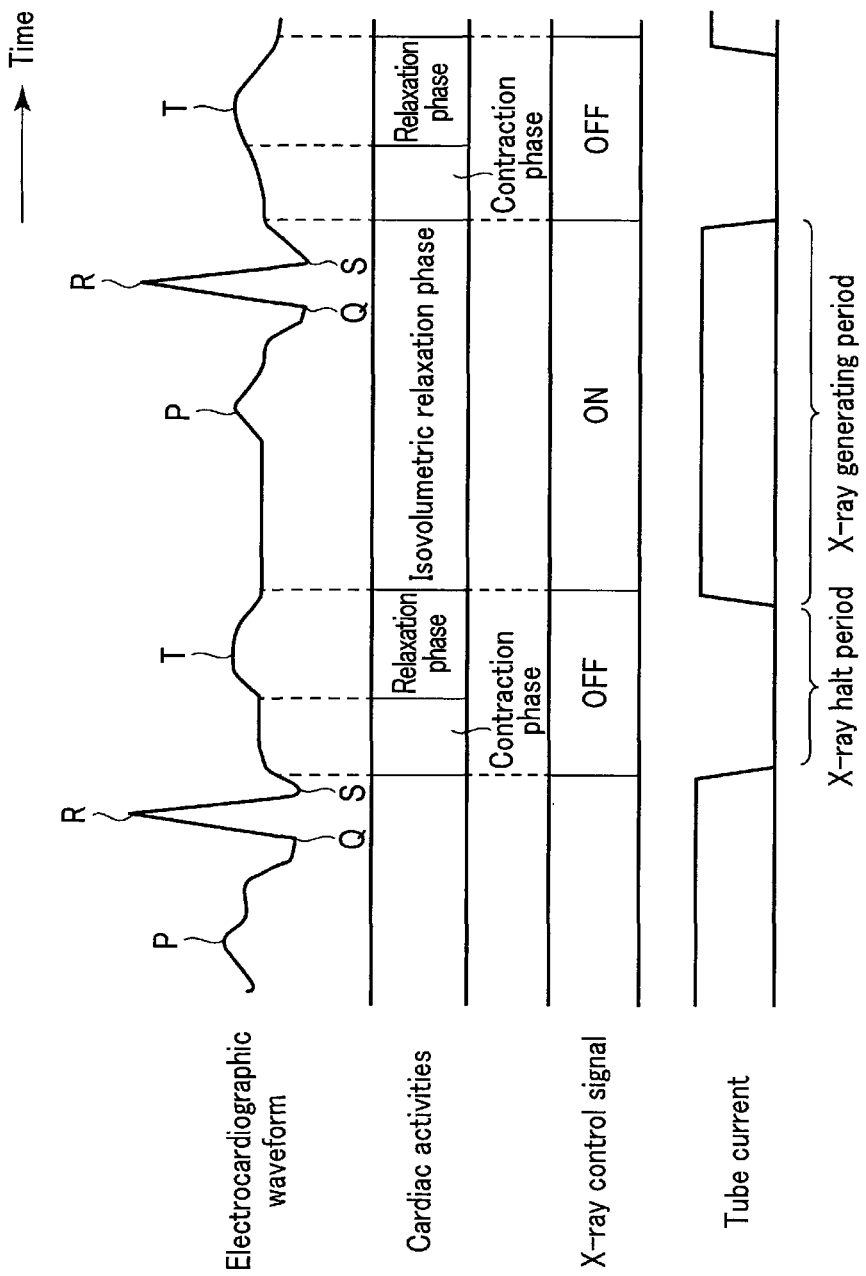
FIG. 2 is a schematic diagram showing a certain example of electrocardiographic waveform data and a method of controlling X-rays during ECG-gated scanning, according to the first embodiment.

FIG. 2 is a schematic diagram showing a certain example of electrocardiographic waveform data obtained by the electrocardiograph 18 and a method of controlling X-rays during ECG-gated scanning. As shown in FIG. 2, it is read from the electrocardiographic waveform data that distinguishing waveforms such as P-waves, Q-waves, S-waves, and T-waves appear in cardiac cycles. In cardiac activities, one heartbeat is categorized into a contraction phase, a relaxation phase, and an isovolumetric relaxation phase. The contraction phase for a systolic activity comes after a substantially definite length of time from the R-wave having the most distinguishing and highest peak. After this contraction phase, the relaxation phase for a diastolic activity comes. The contraction phase and the relaxation phase constitute a period during which a heart undergoes a large size change. The period right after the relaxation phase until right before the contraction phase of the next cardiac cycle is called the isovolumetric relaxation phase, during which the change of the heart size is relatively moderate.

In the ECG-gated scanning, the amount of radiation exposure can be reduced by turning on X-rays to scan during the isovolumetric relaxation phase as a cardiac time phase involving a relatively moderate size change of a heart, and turning off X-rays during the contraction phase and the relaxation phase as cardiac time phases involving a large size change of a heart. Here, turning on X-rays corresponds to switching an X-ray control signal into an ON state, generating X-rays, or emitting X-rays. Turning off X-rays corresponds to switching the X-ray control signal into an OFF state, or halting X-rays.

Accordingly, the heart-rate detection function 34e specifies the cycles of the isovolumetric relaxation phase from the subject P's electrocardiographic waveform data obtained from the electrocardiograph 18, and outputs the cycle information of the isovolumetric relaxation phase to the scan control function 34d. The scan control function 34d causes X-rays to be emitted to the subject P during the isovolumetric relaxation phase so that the heart of the subject P can be scanned at the timing of its moderate size change.

The description will refer back to the processing circuitry 34 in FIG. 1.

A view-number adjustment function 34f includes a function to adjust view numbers in the first scan and the second scan. For example, the view-number adjustment function 34f reads the view number for each of the first scan and the second scan from the memory 31, and sets the view numbers that meet the scan condition. Details of the view-number adjustment function 34f will be made apparent by the descriptions using FIG. 3 and onward. The view-number adjustment function 34f is one example of a view-number adjuster. Also, the region of the subject P scanned during the first scan is one example of a first imaging area, and the region of the subject P scanned during the second scan is one example of a second imaging area.

Each processing function performed by the components of the processing circuitry 34, i.e., the system control function 34a, the preprocessing function 34b, the reconstruction processing function 34c, the scan control function 34d, the heart-rate detection function 34e, and the view-number adjustment function 34f, is stored in the memory 31 in the form of a computer-executable program. The processing circuitry 34 is a processor that realizes functions corresponding to the respective programs by reading and running the programs from the memory 31. In other words, the processing circuitry 34 when having read the programs is furnished with the respective functions shown within the processing circuitry 34 in FIG. 1. While FIG. 1 assumes that the single processing circuitry 34 realizes the processing functions of the system control function 34a, the preprocessing function 34b, the reconstruction processing function 34c, the scan control function 34d, the heart-rate detection function 34e, and the view-number adjustment function 34f, multiple independent processors may be combined to form the processing circuitry 34 so that the processors run programs to realize the functions.

Figure 3:
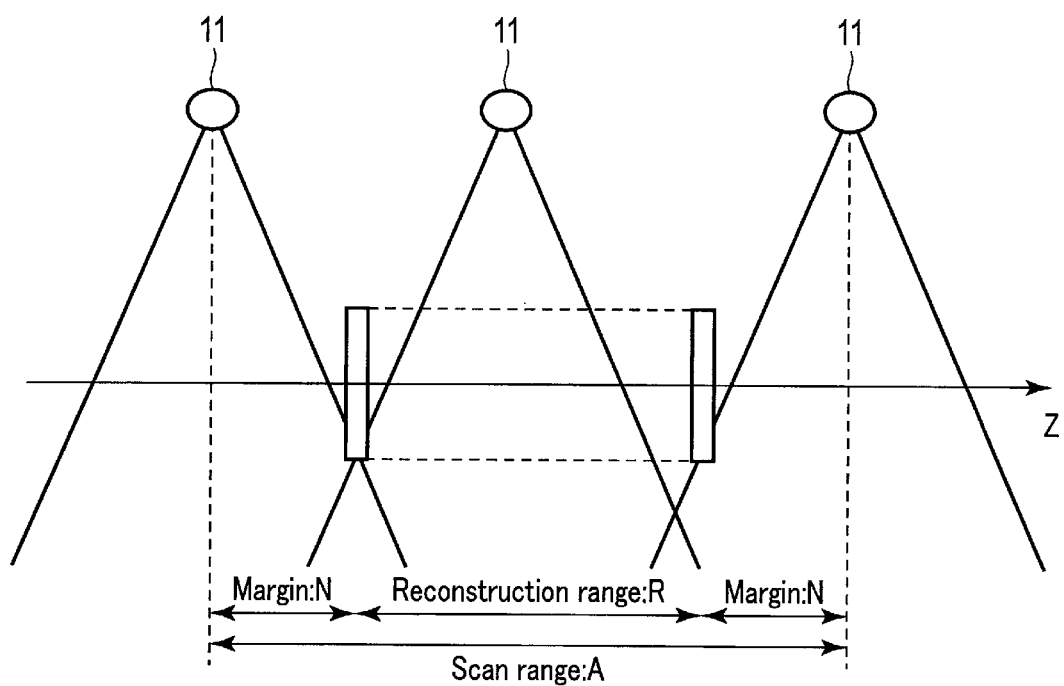
FIG. 3 is a schematic diagram showing a relationship between a reconstruction range and margins during general helical scanning.

FIG. 3 is a schematic diagram showing the relationship between a reconstruction range and margins during general helical scanning. By way of example, FIG. 3 shows the instance where the helical scanning is performed in the Z-axis forward direction. A reconstruction range R here corresponds to an imaging range set by an operator. In the helical-scan operation for the reconstruction range R, scanning is performed over a range including the set reconstruction range R as well as margins N. As such, X-rays during the helical scanning are emitted on the scan range A that is wider than the set reconstruction range R. The margin N corresponds to an area deviated from the imaging range but irradiated with X-rays. The following embodiments each narrow the size of the margin N on at least one side so that X-ray radiations to the area deviated from the imaging range for helical scanning are reduced. The term "scan range" corresponds to "scan area".

FIG. 4 is a schematic diagram showing an overview of the size of one helical-scan pitch (hereinafter, "helical pitch"), a view number, and X-ray radiation timing when a first scan and a second scan according to a comparative example (comparison subject) of the first embodiment are combined and executed. The helical pitch here equals the distance traveled by the couch for the period of one rotation of the X-ray generating device 11 and the X-ray detector 12 in the helical scanning. In the case of a fourth-generation CT, it should be recognized that only the X-ray generating device 11 rotates. The upper portion of FIG. 4 shows the scan range in the subject P. The middle portion of FIG. 4 is a graph to show the changes in helical pitch when the first scan and the second scan are combined and executed, wherein the vertical axis indicates the helical pitch and the horizontal axis indicates the distance in the Z direction. The lower portion of FIG. 4 is a graph to show the timing to emit X-rays when the first scan and the second scan are combined and executed, wherein the vertical axis indicates the amount of emitted X-rays and the horizontal axis indicates time. The arrows additionally shown in the lower portion of FIG. 4 have lengths corresponding to the view numbers of the respective scans. Longer arrows relate to the first scan, and shorter arrows relate to the second scan.

As shown in FIG. 4, when the first scan and the second scan are combined for a scanning operation, scanning is performed on a scan range 40 covering the heart and the other scan ranges, while the helical pitch is modulated. The modulation of the helical pitch in principle indicates, for example, changing the helical pitch by changing the traveling speed of the couch. However, the helical pitch modulation is not limited to this, but may also indicate changing the helical pitch by changing the rotational speed of the X-ray generating device 11 and the X-ray detector 12. In the case of a fourth-generation CT, the understanding as discussed above applies. In the comparative example of FIG. 4, for example, a larger helical pitch is set for a scan range spanning from the head of the subject P up to the scan range 40 that covers the heart, and a smaller helical pitch is set for the heart region. During the helical scanning, the helical pitch gradually decreases as the heart region approaches, as shown in FIG. 4. In this instance, the view number during the helical scanning is kept constant since a view number exceeding a certain value does not contribute to reduction of image noise. However, as an exception, the view number during the second scan for use in the reconstruction of the heart region is decreased so that the temporal resolution will be improved. That is, the reconstruction from the second scan using the same view number as the first scan would result in a low temporal resolution. Thus, the second scan improves the temporal resolution by adopting, for example, a half-scan view number for reconstruction. As such, the view number for the second scan is smaller than the view number for the first scan. Nonetheless, when attention is directed to the moment at which a scanning operation is about to reach a scan area for the second scan during the data acquisition of the first scan, such a configuration of the view number being greater in the first scan than in the second scan would necessitate a time to turn off the X-rays in the course of transition to the second scan, and the transition to the second scan takes some time.

More specifically, the switch from the first scan to the second scan should ideally be done instantly at a time t1 shown in FIG. 4 so that the view number in the ECG-gated scanning starts from the time t1. However, since the view number in the first scan is greater than the view number in the second scan, a time is required before turning off the X-rays for the second scan and the time point to switch off the X-rays must be delayed to a time t2 as shown in FIG. 4. That is, the large view number in the first scan forces the first scan to take some time before completion, resulting in a delay of transition to the X-ray OFF state in the second scan. Accordingly, the purposes of the first and the second embodiments described below will include reducing a radiation dose by cutting the extra time spanning from the time t1 to the time t2 caused due to the first scan, so that the timing to turn off the X-rays for the second scan comes earlier than in the comparative example.

FIG. 5 is a schematic diagram showing further details of the relationship between view numbers when switching from the first scan to the second scan according to the comparative example, having been described with reference to FIG. 4. In FIG. 5, the horizontal axis represents time. The arrows in the figure have lengths corresponding to the view numbers necessary for the respective scans and the time ranges to acquire views. The vertical bar at the center of each arrow corresponds to the timing to acquire a slice image in the reconstruction range. Note that if the horizontal axis in FIG. 5 is taken as a coordinate axis in the Z-axis forward direction, the vertical bar at the arrow's center corresponds to a Z-position of the slice image within the reconstruction range. These interpretations of the horizontal axis and arrows can also apply to each figure in the below descriptions.

In the comparative example as shown in FIG. 5, when executing the first scan up to t1, which is a boundary between the reconstruction range intended for the first scan (first reconstruction range) and the ECG-gated reconstruction range (second reconstruction range), the time range for view acquisition in the first scan is forced to overlap with the ECG-gated reconstruction range. As such, the timing available for turning off the X-rays will be shifted to a time t2 shown in FIG. 5, when performing the intermittent X-ray radiation by the second scan.

Accordingly, the first embodiment aims to shorten the time required up to the completion of the first scan by executing the processing to decrease the view number on the first-scan side in the course of transition from the first scan to the second scan, so as to advance the timing to turn off the X-rays in the second scan.

Figure 6:
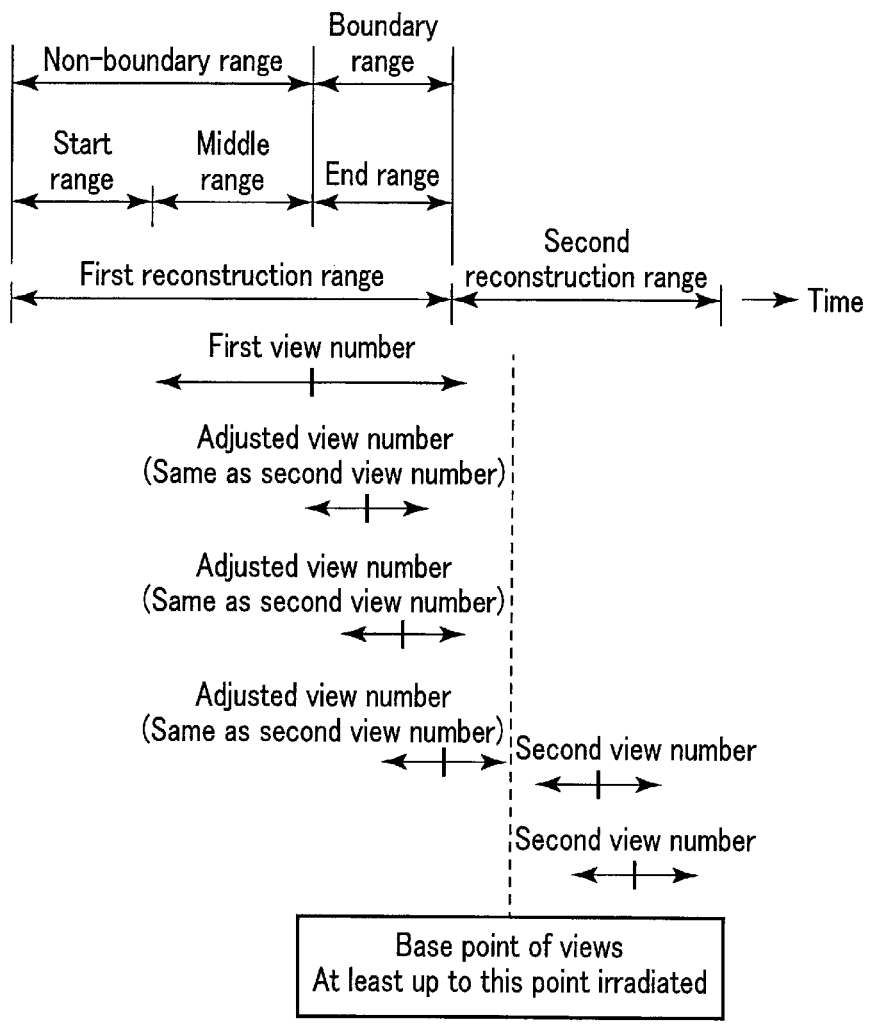
FIG. 6 is a schematic diagram showing an example of a relationship between view numbers in the course of transition from a first scan to a second scan according to the first embodiment.
Figure 7:
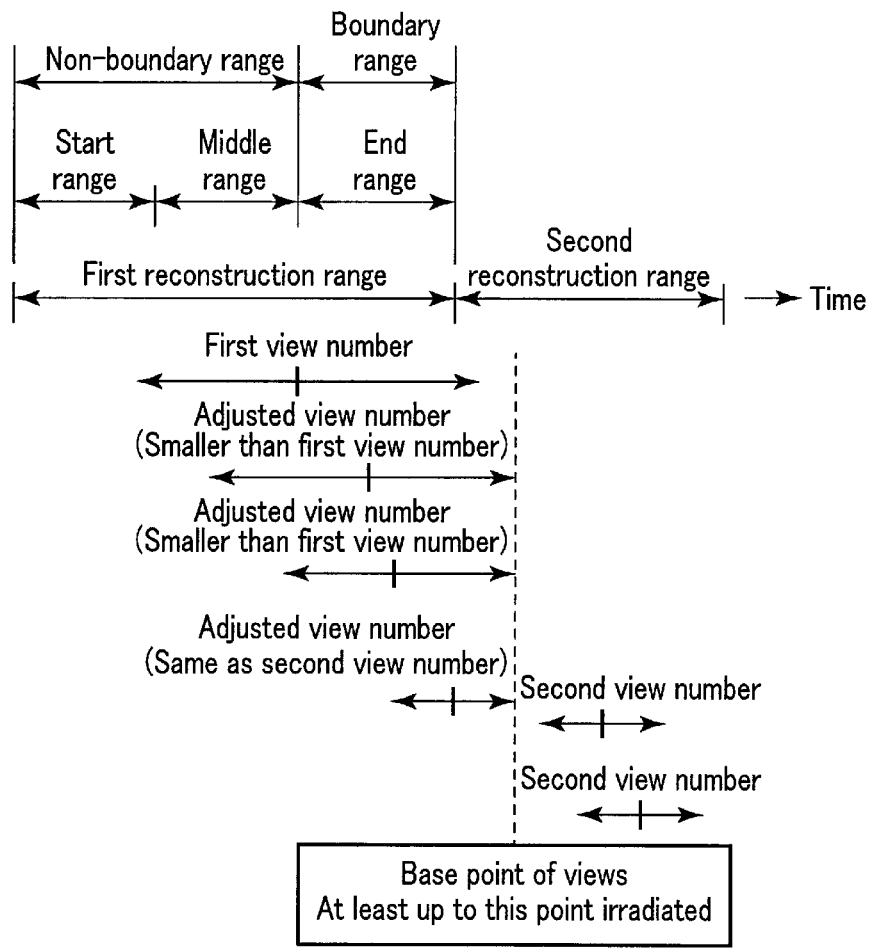
FIG. 7 is a schematic diagram showing another example of the relationship between view numbers in the course of transition from the first scan to the second scan according to the first embodiment.

FIGS. 6 and 7 are schematic diagrams showing examples of the relationship between view numbers in the course of transition from the first scan to the second scan according to the first embodiment. For the first embodiment, the case of decreasing the view number in the first scan to match the view number in the second scan will be described. In the first embodiment, the view-number adjustment function 34*f* reads a view number in the second scan (hereinafter, "second view number") from the memory 31. The view-number adjustment function 34*f* also receives timing information for the ON/OFF of X-rays in the second scan, from the scan control function 34*d*. Using the timing information from the scan control function 34*d*, the view-number adjustment function 34*f* adjusts the view number in the end range of the first reconstruction range (first view number) to decrease in accordance with the second view number, as shown in FIG. 6.

Regarding what is shown in FIGS. 6 and 7, a first imaging range corresponding to the first reconstruction range, a boundary range that is the end range of the first reconstruction range, the first view number for use in the reconstruction processing for a non-boundary range other than the boundary range in the first imaging range, and the view number for use in the reconstruction processing for the boundary range are each set by the processing circuitry 34. The view number for use in the reconstruction processing for the boundary range is set to be smaller than the first view number. Also, the first imaging range has a start range, a middle range, and the end range. If the boundary range is the end range, the non-boundary range other than the boundary range is constituted by the start range and the middle range.

Also, the view-number adjustment function 34*f* may control the view numbers for several slices from the boundary range in the first reconstruction range to match the second view number as shown in FIG. 6, or may control the view numbers in the first scan to decrease in a stepwise manner as shown in FIG. 7. With the stepwise decrease of the view numbers in the first scan as shown in FIG. 7, changes in image quality among the images obtained from the first scan and the second scan can be moderate. Note that, among the arrows representing the view numbers in FIGS. 6 and 7, the topmost arrow in each figure is a view number in the first scan for which a view-number adjustment is not performed. The above control can advance the timing to turn off the X-rays when a process is switched from the first scan to the second scan, as compared to the conventional technique, and allows for the reduction of radiation doses. Also, scanning (number of slices) that should be subjected to the view-number adjustment in the first scan may include, for example, all the scans having a time range that would be forced to overlap with the timing to start the second scan (corresponding to the base point of views in FIGS. 6 and 7) if the use of a normal first-scan view number and acquisition of the same are assumed.

[Operations]

Figure 8:
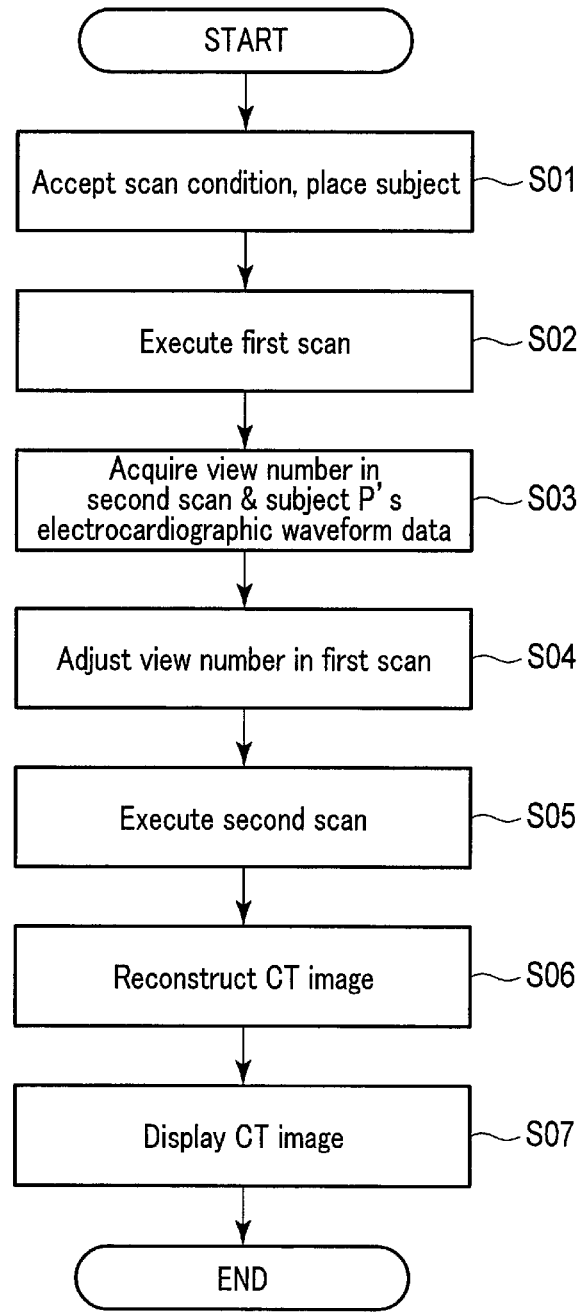
FIG. 8 is a flowchart showing a certain example of processing according to the first embodiment.

A certain example of the processing of the X-ray CT apparatus 100 having the above configurations will now be described with reference to the flowchart in FIG. 8.

First, the X-ray CT apparatus 100 accepts a scan condition from an operator via the input interface 33. For example, the input interface 33 accepts scan ranges for the first scan and the second scan. The system control function 34a of the processing circuitry 34 sets a first imaging range within the imaging range for the helical scanning, and sets at least one of a start range and an end range in the first imaging range as a boundary range, based on the operation on the input interface 33, for example. The processing circuitry 34 also sets a first view number for use in the reconstruction processing for a non-boundary range other than the boundary range in the first imaging range, and sets a view number for use in the reconstruction processing for the boundary range to be smaller than the first view number. The processing circuitry 34 also sets a second imaging range adjacent to the boundary range on the side opposite to the non-boundary range, sets a second view number for use in the reconstruction processing for the second imaging range to be smaller than the first view number, and sets a minimum view number for use in the reconstruction processing for the boundary range to be equal to the second view number. Further, the processing circuitry 34 sets the scan condition so that a first helical pitch is used for the non-boundary range, a second helical pitch that is narrower than the first helical pitch is used for the second imaging range, and a helical pitch modulated between the first helical pitch and the second helical pitch is used for the boundary range. These scan plan settings may utilize scanogram images taken prior to the first and second scans. Also, a subject P is placed on the couch top 17 by the operator, etc. (step S01).

Next, the scan control function 34d reads the scan plan including the scan condition accepted by the input interface 33 and executes the first scan. At this time, the gantry driving device 19 moves the couch top 17 at a speed that accords with the first scan (first speed). In the first scan, regions of the subject P, for example, regions on the side of the head as viewed from the heart (step S02), are scanned.

Next, the view-number adjustment function 34f reads the imaging range for the second scan (second imaging range) accepted via the input interface 33, and the second view number from the memory 31. The heart-rate detection function 34e reads the subject P's electrocardiographic waveform data obtained by the electrocardiograph 18. At this time, the scan control function 34d extracts, for example, a period applicable to the isovolumetric relaxation phase from the electrocardiographic waveform data given from the heart-rate detection function 34e, and sets this period as an X-ray ON period and sets the other periods as X-ray OFF periods (step S03). The step S03 may precede the step S02.

Next, the view-number adjustment function 34f adjusts the view number on the first-scan side (first view number) to match the view number in the second scan (second view number) during a transition period from the first scan to the second scan. At this time, the gantry driving device 19 moves the couch top 17 at a speed that accords with the second scan (second speed). In this relation, the transition period from the first scan to the second scan indicates a time period for the helical pitch to involve changes to decrease in the course of transition from the first scan to the second scan. The transition period corresponds to the period of the boundary range. In the present embodiment, the view-number adjustment function 34f adjusts the view number for the boundary range in the first scan to decrease so that it conforms to the second view number (step S04).

Next, the scan control function 34d executes the second scan for the second-scan imaging range, with the second view number. Since the view number for the boundary range in the first scan has conformed to the second view number in step S04, it is possible to perform a control to instantly turn off the X-rays upon start of the second scan. At this time, the scan control function 34d executes the second scan while controlling the ON/OFF timing of X-rays using the electrocardiographic waveform data given from the heart-rate detection function 34e (step S05).

Detection data acquired through the first scan and the second scan is, for example, converted into sinogram data at the DAS 16 and transmitted to the console unit 30. In the console unit 30, the obtained sinogram data is subjected to preprocessing by the preprocessing function 34b so that projection data is generated. The generated projection data is subjected to reconstruction processing by the reconstruction processing function 34c so that CT images are generated. Note that since the first scan and the second scan are performed with different view numbers for the projection data as described earlier, different view numbers are used in the reconstruction processing such that a smaller view number is set for the second scan. Therefore, CT images obtained from the second scan have a higher temporal resolution than CT images obtained from the first scan (step S06).

Lastly, the system control function 34a displays the CT images given by the reconstruction processing function 34c on the display 32 (step S07).

According to the first embodiment described above, it is possible to advance the X-ray OFF timing in the second scan when performing a scanning operation that combines the first scan and the second scan, thereby allowing for the reduction of radiation doses on the subject P.

More specifically, the first embodiment sets a first imaging range within the imaging range for the helical scanning, and sets at least one of a start range and an end range in the first imaging range as a boundary range. It also sets a first view number for use in the reconstruction processing for a non-boundary range other than the boundary range in the first imaging range, and sets a view number for use in the reconstruction processing for the boundary range to be smaller than the first view number. Accordingly, with the configuration to set the view number for use in the reconstruction processing for the boundary range to decrease, it narrows the margin size that deviates from the imaging range so that X-ray radiations to the area deviated from the imaging range for the helical scanning can be reduced. This effect is attainable in both the case of VHP scanning involving the first scan and the ECG-gated scanning, and the case of normal helical scanning involving only the first scan.

Also, the first embodiment sets a second imaging range adjacent to the boundary range on the side opposite to the non-boundary range, sets a second view number for use in the reconstruction processing for the second imaging range to be smaller than the first view number, and sets a minimum view number for use in the reconstruction processing for the boundary range to be equal to the second view number. Accordingly, with the configuration to set the minimum view number for use in the reconstruction processing for the boundary range to be equal to the second view number, it can further narrow the margin size as compared to the case of setting the minimum view number to be larger than the second view number, and the X-ray radiations to the area deviated from the imaging range can be further reduced.

Also, the first embodiment sets a scan condition so that a first helical pitch is used for the non-boundary range, a second helical pitch that is narrower than the first helical pitch is used for the second imaging range, and a helical pitch modulated between the first helical pitch and the second helical pitch is used for the boundary range. Accordingly, it can execute the VHP scanning that provides the effects discussed above.

Also, according to the first embodiment, the view number for use in the reconstruction processing for the boundary range may be set so that it decreases in a stepwise manner. This can smooth the variation in quality of the images from the boundary range.

According to the first embodiment, the view number for use in the reconstruction processing for the boundary range and the second view number may also be set to be the same value. This can facilitate the setting of the view number for use in the reconstruction processing for the boundary range as compared to the case of setting it to decrease in a stepwise manner.

Second Embodiment

The first embodiment has been described for the cases of decreasing the view number in the end portion of the first scan to match the second view number in the course of transition from the first scan to the second scan. The second embodiment will be described for the cases of switching between the adjustment and non-adjustment of the view number in the end portion of the first scan.

In the second scan, X-rays are turned on and off in accordance with the size changes of a heart as shown in FIG. 2 so that the radiation doses are reduced. As such, the X-ray OFF timing may not always come upon transition from the first scan to the second scan, and there can be instances where the operation proceeds to the second scan while the X-ray emission is kept ON. In such instances, since the X-rays stay in the ON state at the time domain for the second scan, the view number in the end portion of the first scan need not be decreased. Therefore, in the second embodiment, when an electrocardiographic waveform is received from the electrocardiograph 18 in the course of transition from the first scan to the second scan, and if it is found that the view number in the end portion of the first scan needs to be adjusted, the view-number adjustment as described in the first embodiment is performed. If the view-number adjustment for the end portion of the first scan is found unnecessary, a larger view number is adopted for the first scan to cover the X-ray ON period in the second scan so that the spatial resolution of the first scan is upgraded.

FIG. 9 is a schematic diagram showing the relationship between view numbers when the first scan and the second scan according to the second embodiment are combined. More specifically, FIG. 9 shows the instance where the view number in the first scan is not adjusted to conform to the second view number, but the view number in the first scan is obtained by including the X-ray ON period in the second scan.

As shown in FIG. 2, the X-ray ON/OFF periods in the second scan are determined based on electrocardiographic waveform data. Thus, the timing to switch from the first scan to the second scan could encounter the X-ray ON timing in the second scan, such as coming of the isovolumetric relaxation phase of a heart. In this instance, the X-ray OFF timing is delayed by as much as a time corresponding to the initial X-ray ON period ΔT of the second scan as shown in FIG. 9.

For example, the view-number adjustment function 34f obtains the patient P's electrocardiographic waveform data from the external electrocardiograph 18, and based on this electrocardiographic waveform data, determines whether or not the view number for use in the reconstruction processing for the boundary range should be adjusted. Also, if the second imaging range right after the boundary range coincides with the timing of X-ray generation, the view-number adjustment function 34f extends the view number for use in the reconstruction processing for the boundary range based on the period to generate the X-rays right after the boundary range.

More specifically, the view-number adjustment function 34f reads the subject P's electrocardiographic waveform data from the heart-rate detection function 34e, and if the electrocardiographic waveform is found indicative that the X-rays should be turned on, it extends the range for acquisition with the view number on the first-scan side into the range on the second-scan side. If the electrocardiographic waveform is found indicative that the X-rays should be turned off, the view-number adjustment function 34f adjusts the view number in the end portion of the first scan to match the second view number as in the first embodiment.

The view-number adjustment function 34f according to the second embodiment, while including the functions described for the first embodiment, additionally reads the information for the X-ray ON/OFF timing in the second scan from the scan control function 34d, and determines whether or not the view-number adjustment for the first scan in the course of transition from the first scan to the second scan is required.

The other configurations are the same as the first embodiment.

Figure 10:
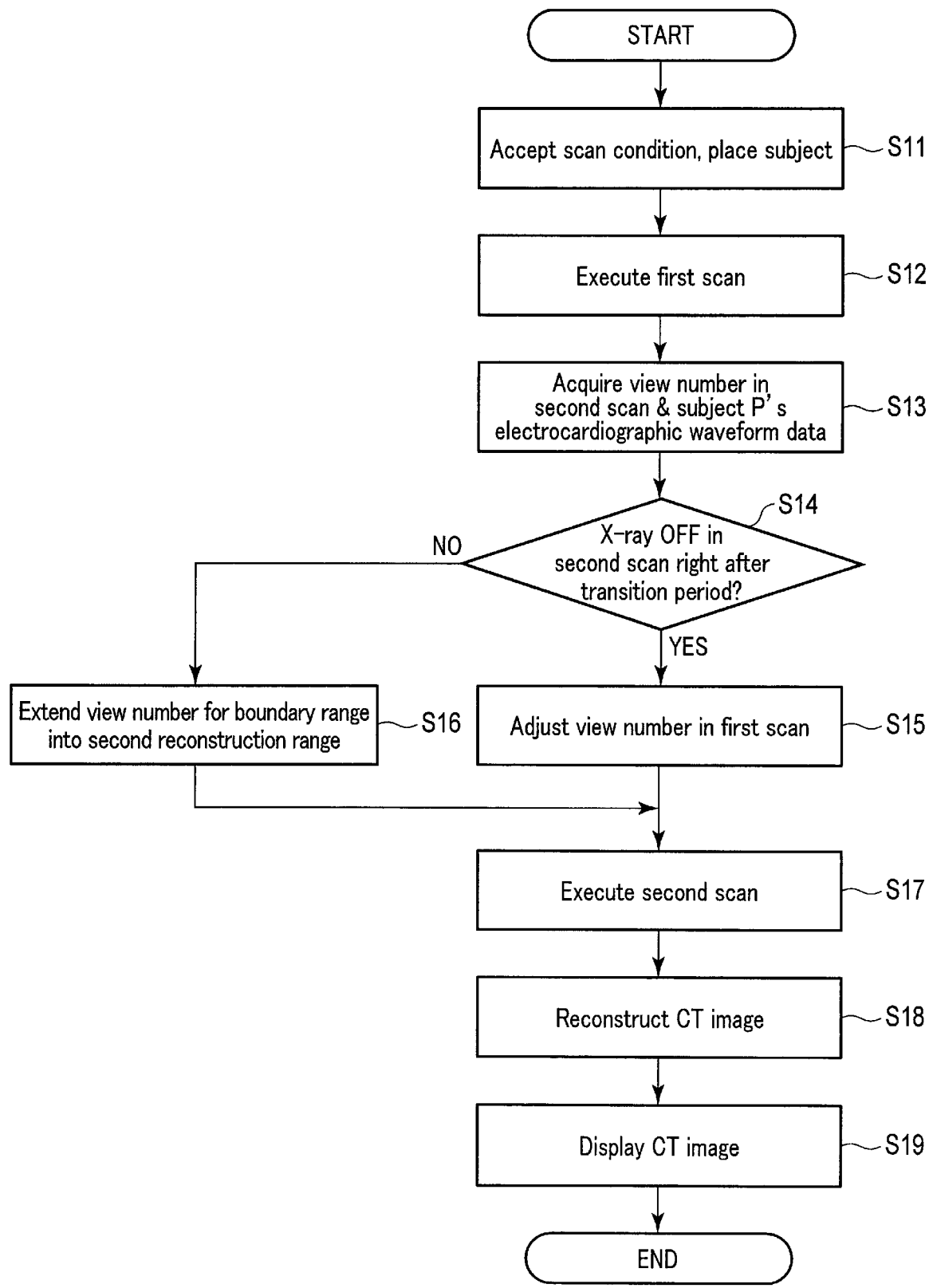
FIG. 10 is a flowchart showing a certain example of processing according to the second embodiment.

A certain example of the processing of the X-ray CT apparatus 100 having the above configurations will now be described with reference to the flowchart in FIG. 10. Note that the processing contents in steps S11 to S13 and S17 to S19 are the same as the respective steps S01 to S03 and S05 to S07 shown in the flowchart in FIG. 8 for the first embodiment, and therefore, their descriptions will be omitted.

The view-number adjustment function 34f accepts, from the scan control function 34d, information for the X-ray ON/OFF timing in the second scan that immediately follows the period of transition from the first scan to the second scan. Examples available as this information include information indicating the timing to switch between X-ray ON/OFF periods, in which the isovolumetric relaxation phase according to the subject P's electrocardiographic waveform data from the external electrocardiograph 18 is associated with the X-ray ON period and the phases other than the isovolumetric relaxation phase are associated with the X-ray OFF period. The view-number adjustment function 34f reads this information to determine whether or not the view number in the first scan should be adjusted (step S14). At this time, if the second scan right after the transition period (boundary range) coincides with the X-ray ON timing (step S14, NO), it determines that the view-number adjustment in the first scan is unnecessary so that the data acquisition at the X-ray ON timing in the second scan may continue, and extends the view number to conform to the view number in the first scan (step S16). If the second scan right after the transition period coincides with the X-ray OFF timing (step S14, YES), it determines that the view-number adjustment in the first scan is necessary, and adjusts the view number in the end portion of the first scan to decrease in accordance with the view number in the second scan as in the first embodiment (step S15).

According to the second embodiment described above, it is possible to cope with the first-to-second scan transition period corresponding to either the X-ray ON period or the X-ray OFF period such that: if the immediately succeeding period is the X-ray ON period, the second embodiment does not decrease the view number in the first scan so as to enable the first scan to provide images of a high spatial resolution; and if the immediately succeeding period is the X-ray OFF period, the second embodiment adjusts the view number in the first scan to decrease in accordance with the second view number so as to allow the time required to turn off the X-rays to be shortened and to allow the radiation dose to be reduced.

Also, according to the second embodiment, it is possible to advance the X-ray OFF timing in the second scan by decreasing the view number for the boundary range to match the second view number in the second scan, as in the first embodiment.

Note that the above descriptions for the first and second embodiments have assumed that the second scan is performed after the first scan. However, the VHP scanning is executed along the longitudinal direction of the couch top 17 and it covers a wide range of the subject P including the heart region. Thus, the second scan may be performed prior to the first scan. In such instances, the view-number adjustment for the first scan may also be performed at the timing to switch from the second scan to the first scan, in a manner similar to the timing to switch from the first scan to the second scan.

Third Embodiment

The first and second embodiments have been described for the cases of executing both the first scan and the second scan. The third embodiment will be described for the cases of normal helical scanning that involves only the first scan, without the second scan (ECG-gated scanning). In the cases of this embodiment, the system control function 34a performs one of the following (i) to (iii) types of processing when setting at least one of a start range and an end range in the first imaging range as a boundary range.

(i) Processing to set only the start range as the boundary range.

(ii) Processing to set only the end range as the boundary range.

(iii) Processing to set both the start range and the end range as the boundary ranges.

Descriptions will be given, taking the processing (iii) as an example. However, this is not a limitation and the processing (i) or (ii) is also applicable. Also, while the helical scanning assumed in this embodiment is not VHP scanning, it may be the VHP scanning.

Figure 11:
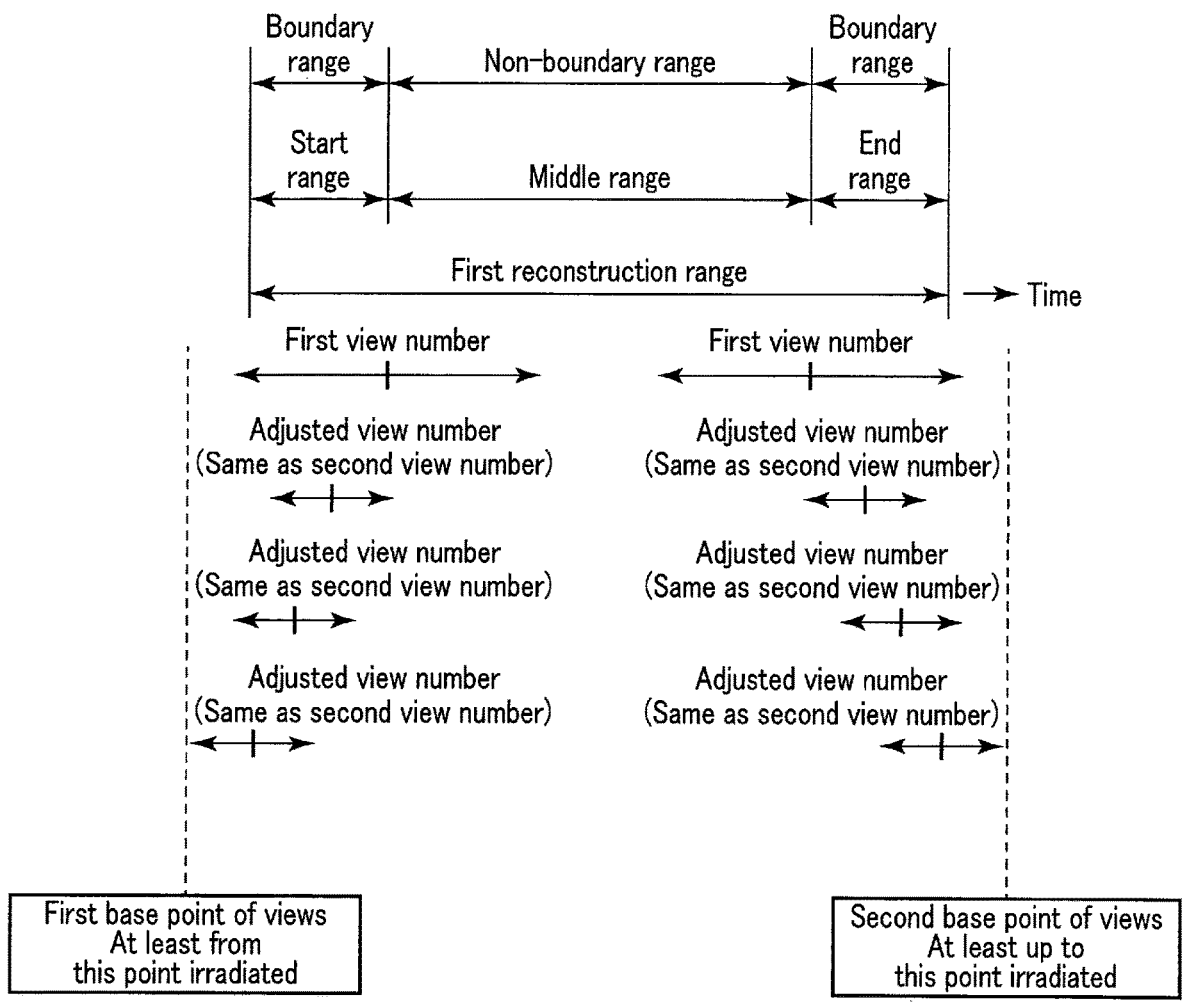
FIG. 11 is a schematic diagram showing an example of a relationship between view numbers in a first scan according to a third embodiment.
Figure 12:
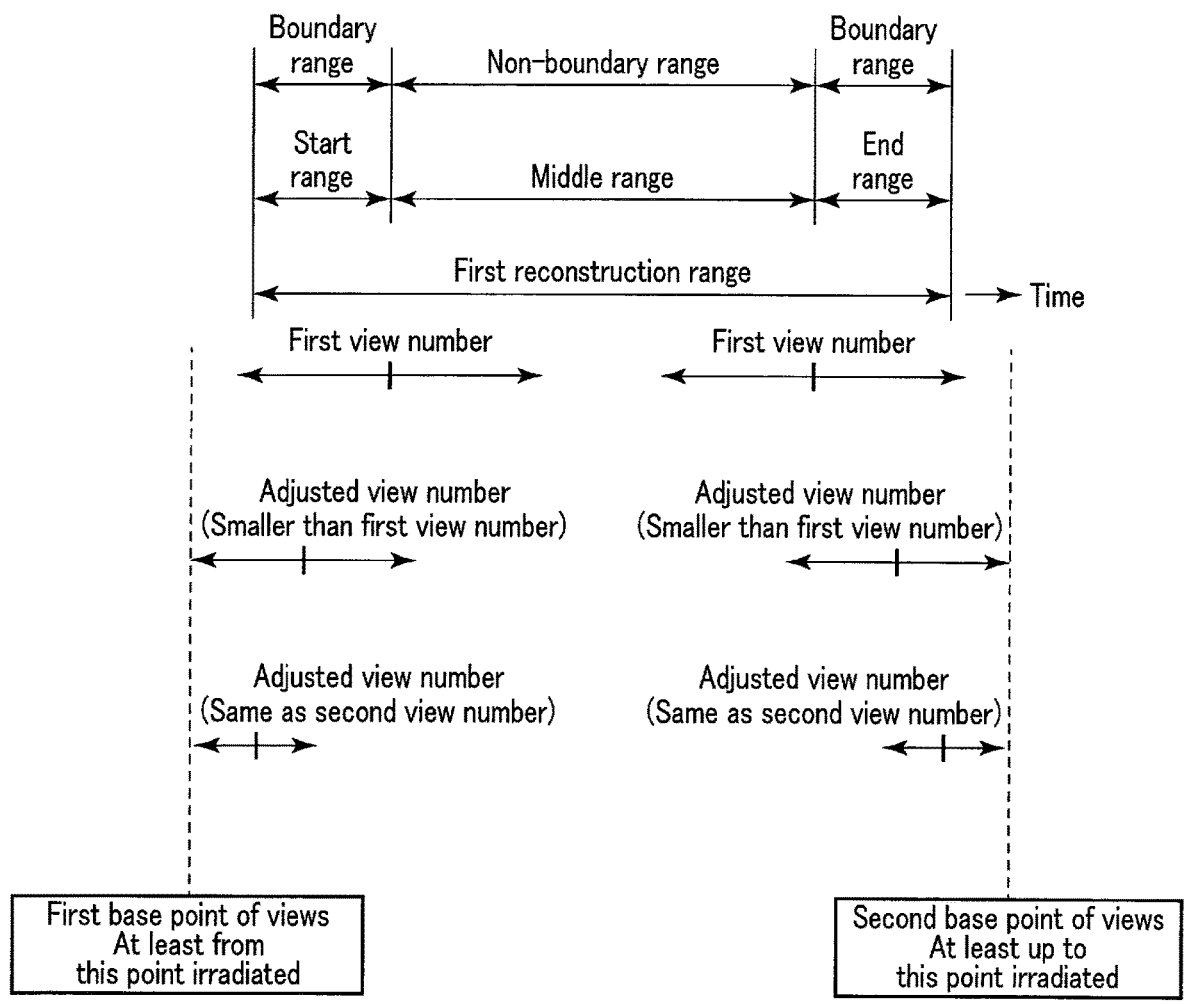
FIG. 12 is a schematic diagram showing another example of the relationship between view numbers in the first scan according to the third embodiment.

FIGS. 11 and 12 are schematic diagrams showing examples of the relationship between view numbers in the first scan. In the third embodiment, the first imaging range corresponding to the first reconstruction range, two boundary ranges as the respective start and end ranges in the first reconstruction range, the first view number for use in the reconstruction processing for a non-boundary range other than the boundary ranges, and the view number for use in the reconstruction processing for the boundary ranges are set by the system control function 34a. The view number for use in the reconstruction processing for the boundary ranges is set to be smaller than the first view number. Also, the first imaging range has start, middle, and end ranges. When the boundary ranges are the respective start and end ranges, a non-boundary range other than the boundary ranges is the middle range.

In this instance, the boundary ranges may be set by, for example, designating a start range having a predetermined length and an end range having a predetermined length as the respective boundary ranges. The value of the "predetermined length" may be set in the form of, for example, presetting in a parameter file in the memory 31. Also, scanning (number of slices) that should be subjected to the view-number change in the start range may include, for example, all the scans having a time range that would be forced to overlap with the timing to start the first scan (corresponding to the first base point of views in FIGS. 11 and 12) if the use of the first view number and acquisition of the same are assumed. Likewise, scanning (number of slices) that should be subjected to the view-number change in the end range may include, for example, all the scans having a time range that would be forced to overlap with the timing to finish the first scan (corresponding to the second base point of views in FIGS. 11 and 12) if the use of the first view number and acquisition of the same are assumed. The system control function 34a may set the view number for use in the reconstruction processing for the boundary ranges so that it is changed at once as shown in, for example, FIG. 11. The system control function 34a may also set the view number for use in the reconstruction processing for the boundary ranges so that it is changed in a stepwise manner as shown in, for example, FIG. 12. In FIGS. 11 and 12, the minimum view number for use in the reconstruction processing for the boundary ranges is called a second view number. Note that, unlike in the first and second embodiments, the second view number in the context of the third embodiment does not mean the view number for a second scan as the third embodiment involves no second scan.

The method of setting the first view number and the second view number may include setting view-number values, or setting percentage values corresponding to the view numbers. To adopt the percentage values, for example, the value corresponding to the first view number may be set as 100% when this first view number is assumed to be a view number under the full-scan reconstruction mode. Similarly, when the second view number is assumed to be a view number under the half-scan reconstruction mode, the value corresponding to this second view number may be set as 0%.

The other configurations are the same as the first embodiment.

Figure 13:
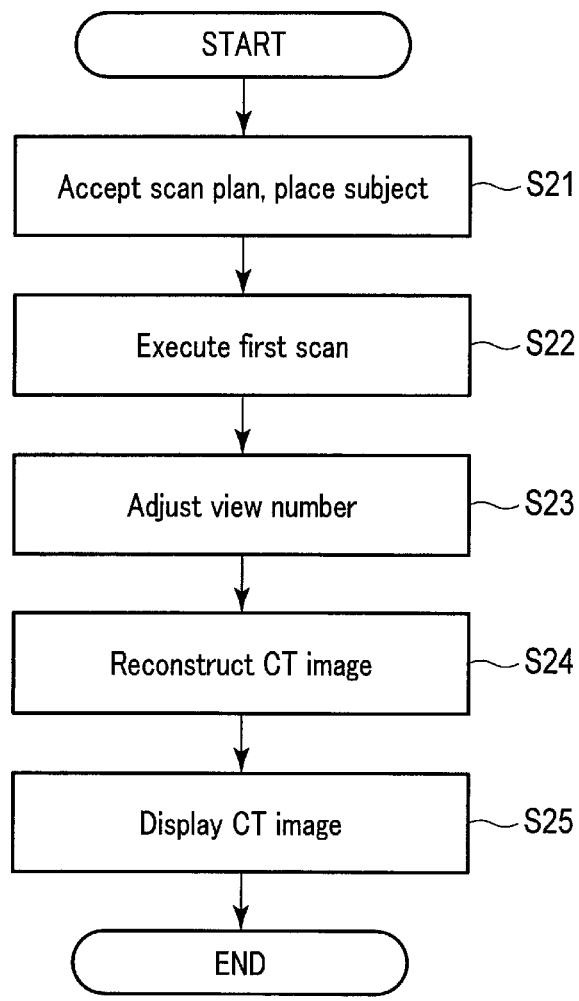
FIG. 13 is a flowchart showing a certain example of processing according to the third embodiment.

A certain example of the processing of the X-ray CT apparatus 100 having the above configurations will now be described with reference to the flowchart in FIG. 13. First, the X-ray CT apparatus 100 accepts a scan plan from an operator via the input interface 33. For example, the system control function 34a of the processing circuitry 34 sets a first imaging range within the imaging range for the helical scanning, and sets both of a start range and an end range in the first imaging range as boundary ranges, based on the operation on the input interface 33. The processing circuitry 34 also sets a first view number for use in the reconstruction processing for a middle range other than the boundary ranges in the first imaging range, and sets a view number for use in the reconstruction processing for the boundary ranges to be smaller than the first view number. The processing circuitry 34 sets the minimum view number for use in the reconstruction processing for the boundary ranges as a second view number. These scan-plan settings may utilize scanogram images taken prior to the first scan. Also, a subject P is placed on the couch top 17 by the operator, etc. (step S21).

Next, the scan control function 34d executes the first scan based on the scan plan accepted by the input interface 33 (step S22). At this time, the gantry driving device 19 moves the couch top 17 at a speed that accords with the first scan. The view-number adjustment function 34f adjusts the view number from the view base point of the first scan and in the start range, so that it increases to match the first view number for the middle range. Thereafter, the view-number adjustment function 34f adjusts the view number in the end range so that it becomes smaller than the first view number (step S23). The first scan ends accordingly.

Detection data acquired through the first scan is, for example, converted into sinogram data at the DAS 16 and transmitted to the console unit 30. In the console unit 30, the obtained sinogram data is subjected to preprocessing by the preprocessing function 34b so that projection data is generated. The generated projection data is subjected to reconstruction processing by the reconstruction processing function 34c so that CT images are generated. Note that since the first scan in the boundary ranges use a view number different from the view number in the middle range for projection data, different view numbers are used in the reconstruction processing such that a smaller view number is set for the boundary ranges. Thus, CT images from the boundary ranges have a higher temporal resolution and a lower image quality than CT images from the middle range (step S24).

Lastly, the system control function 34a displays the CT images given by the reconstruction processing function 34c on the display 32 (step S25).

The third embodiment described above sets a first imaging range within the imaging range for the helical scanning, and sets at least one of a start range and an end range in the first imaging range as a boundary range. It also sets a first view number for use in the reconstruction processing for a non-boundary range other than the boundary range or ranges in the first imaging range, and sets a view number for use in the reconstruction processing for the boundary range or ranges to be smaller than the first view number. Accordingly, it can reduce the X-ray radiations to the areas deviated from the imaging range in the cases of normal helical scanning that involve only the first scan.

Also, according to the third embodiment, the view number for use in the reconstruction processing for the boundary range or ranges may be set so that it is changed in a stepwise manner. This can smooth the variation in quality of the images from the boundary range or ranges.

Also, according to the third embodiment, the view number for use in the reconstruction processing for the boundary range or ranges may be set so that it is changed at once. This can facilitate the setting of the view number as compared to the case of setting it to change in a stepwise manner.

(Modification)

A modification of the third embodiment will be described. In this modification, the system control function 34a is modified so that it is adapted to set a boundary range based on examination regions. The term "examination region" may be replaced with other terms as appropriate, such as "region of an examination subject", "imaging region", and "region of imaging target". Also, the other configurations are the same as the third embodiment.

More specifically, when dealing with an examination region that tolerates a low image quality in either the start range or the end range, the system control function 34a, in accordance with this examination region, sets one of the start range and the end range as the boundary range. For example, if the examination region is a lower extremity and the end range is a tiptoe, the system control function 34a sets the end rage as the boundary range in accordance with this examination region. If, depending on a hospital, the examination region is a lower extremity and the start range is a tiptoe, it sets the start range as the boundary range in accordance with the examination region. Also, for example, if the examination region is an upper extremity and the start range is a fingertip, the system control function 34a sets the start range as the boundary range in accordance with the examination region. If, depending on a hospital, the end range is a fingertip, it sets the end range as the boundary range in the manner similar to the above. Further, for example, if the examination region is constituted by a chest region and an abdominal region, it sets both of the start range and the end range as the boundary ranges in accordance with this examination region. Alternatively, in this example of the examination region constituted by a chest region and an abdominal region, it sets no boundary ranges (the boundary-range setting is turned off) in accordance with the examination region.

Such a configuration can be easily realized by, for example, storing information that associates an examination region with at least one of the start range and the end range in advance, and setting the boundary range by the system control function 34a based on the information.

According to the modification as above, with the configuration to set at least one of the start range and the end range as the boundary range based on the examination region, it is possible to reduce the work of setting the boundary ranges, in addition to providing the effects of the third embodiment.

Fourth Embodiment

Figure 14:
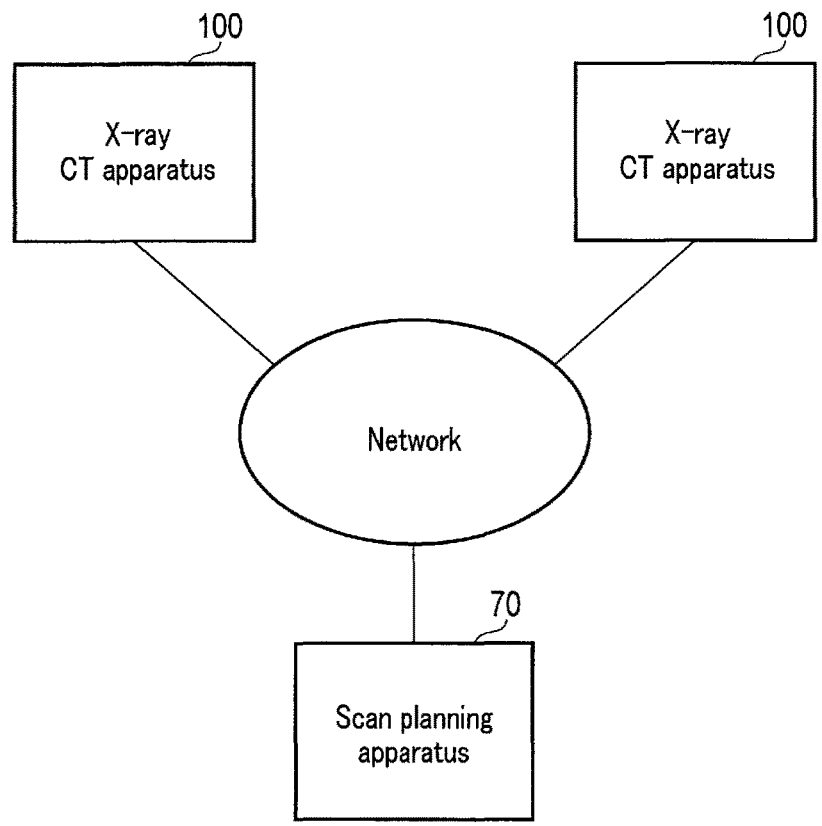
FIG. 14 is a block diagram showing an overview configuration of an X-ray CT system according to a fourth embodiment.

FIG. 14 is a block diagram showing an overview configuration of an X-ray CT system according to the fourth embodiment. This X-ray CT system includes one or more X-ray CT apparatuses 100, and a scan planning apparatus 70. The one or more X-ray CT apparatuses 100 and the scan planning apparatus 70 are communicably connected via a network.

The X-ray CT apparatuses 100 perform CT examinations in accordance with a scan plan informed from the scan planning apparatus 70. The X-ray CT apparatuses 100 according to the fourth embodiment each have a configuration in which the function to set scan plans is omitted from the processing circuitry 34 shown in FIG. 1.

The scan planning apparatus 70 is a computer apparatus that sets scan plans for the helical scanning of subjects and informs the X-ray CT apparatuses 100 of the set scan plans. The terms "scan plan" and "scan planning apparatus" may be replaced with other terms such as "imaging plan" and "image planning apparatus".

Figure 15:
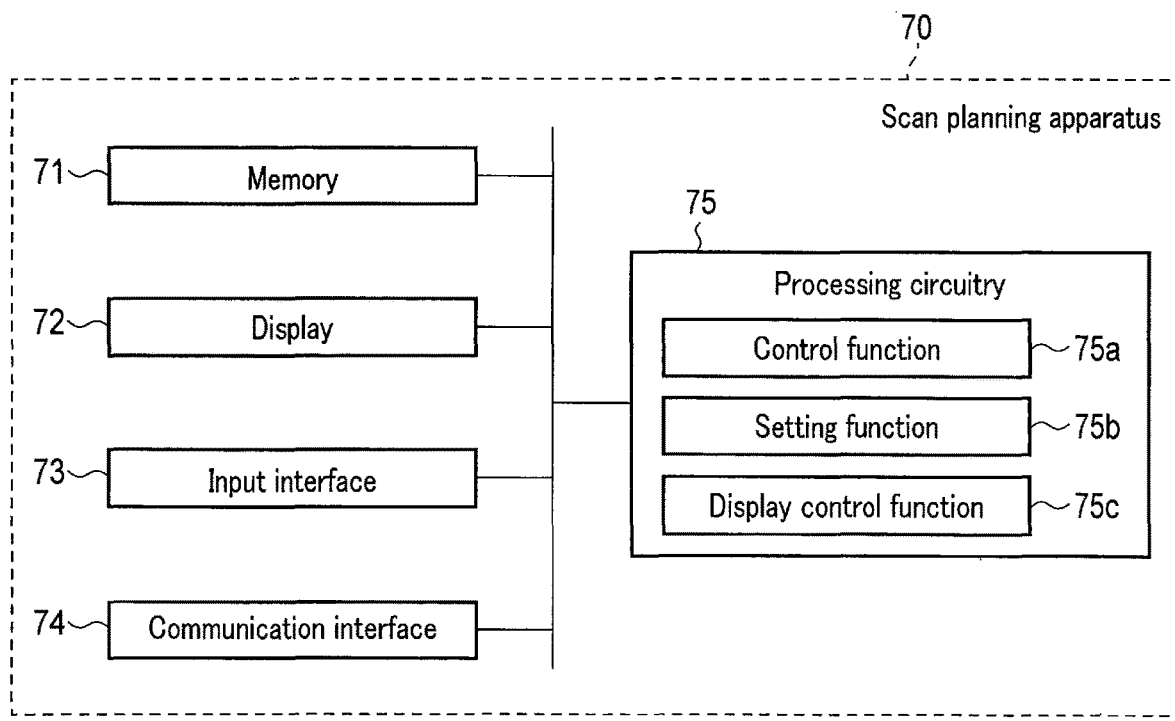
FIG. 15 is a block diagram showing an overview configuration of a scan planning apparatus according to the fourth embodiment.

FIG. 15 is a block diagram showing an overview configuration of the scan planning apparatus 70. The scan planning apparatus 70 includes a memory 71, a display 72, an input interface 73, a communication interface 74, and processing circuitry 75. The memory 71, the display 72, the input interface 73, the communication interface 74, and the processing circuitry 75 perform data communication via a bus.

The memory 71 is a storage device such as a hard disk drive (HDD), a solid state drive (SSD), or an integrated circuit storage device adapted to store various types of information. Other than an HDD, SSD or the like, the memory 71 may be a portable storage device such as a CD, a DVD, or a flash memory, or a driving apparatus that reads and writes various information in cooperation with semiconductor memory devices, etc. including a RAM. The memory 71 stores, for example, imaging ranges corresponding to the respective reconstruction ranges for the first scan and the second scan, boundary ranges, view numbers, helical pitches, FOVs, and control programs and tables for the present embodiment. The memory 71 is one example of a storage.

The display 72 displays various information. For example, the display 72 outputs scan plans set by the processing circuitry 75, GUIs to accept various operations from operators, and so on. As the display 72, for example, a liquid crystal display, a CRT display, an organic EL display, a plasma display, or any other given display may be adopted. The display 72 is one example of a display.

The input interface 73 accepts various input operations from operators, converts the accepted input operations into electrical signals, and outputs them to the processing circuitry 75. As the input interface 73, for example, a mouse, a keyboard, a trackball, switches, buttons, a joystick, a touch pad, and a touch-panel display are available as appropriate. However, the input interface 73 in this embodiment is not limited to a member with a physical operational component such as a mouse, a keyboard, a trackball, switches, buttons, a joystick, a touch pad, and a touch-panel display. That is, the examples of the input interface 73 also include processing circuitry for electrical signals that receives an electrical signal corresponding to an input operation from an external input device separate from the apparatus, and outputs the electrical signal to the processing circuitry 75. The input interface 73 is one example of an inputter.

The communication interface 74 is communication circuitry that performs data communication with the X-ray CT apparatuses 100 via wires (not shown) or wirelessly. For example, the communication interface 74 notifies the X-ray CT apparatuses 100 of the scan plan set by a setting function 75b. The communication interface 74 is one example of a communicator. The communicator may also be called a notifier.

The processing circuitry 75 controls operations of the entire scan planning apparatus 70 according to the electrical signals of the input operations, output from the input interface 73. For example, the processing circuitry 75 includes, as hardware resources, a processor such as a CPU, an MPU and a GPU, and a memory such as a ROM and a RAM. The processing circuitry 75 implements a control function 75a, the setting function 75b, a display control function 75c, etc. by a processor adapted to run a program expanded on the memory. The control function 75a may include the setting function 75b. Each function is not limited to the implementation by a single processing circuit. Multiple independent processors may be combined to form processing circuitry to have each processor run the program, so that each function will be realized.

In the control function 75a, the processing circuitry 75 controls each function of the processing circuitry 75 based on the input operations accepted from operators via the input interface 73, in a manner similar to the first embodiment. The control function 75a is one example of a controller.

In the setting function 75b, the processing circuitry 75 sets the scan plan by setting a first imaging range within the imaging range for the helical scanning, setting at least one of a start range and an end range in the first imaging range as a boundary range, setting a first view number for use in the reconstruction processing for a non-boundary range other than the boundary range in the first imaging range, and setting a view number for use in the reconstruction processing for the boundary range to be smaller than the first view number. In this setting function 75b, the processing circuitry 75 may set the view number for the boundary range to decrease in a stepwise manner.

In the setting function 75b, the processing circuitry 75 may also set the scan plan so that it includes a second imaging range adjacent to the boundary range on the side opposite to the non-boundary range, and sets a second view number for use in the reconstruction processing for the second imaging range to be equal to or smaller than a minimum view number for use in the reconstruction processing for the boundary range. In the setting function 75b, the processing circuitry 75 may set the view number for use in the reconstruction processing for the boundary range and the second view number to be the same value.

In the setting function 75b, the processing circuitry 75 may set the scan plan so that a first helical pitch is used for the non-boundary range, a second helical pitch that is narrower than the first helical pitch is used for the second imaging range, and a helical pitch modulated between the first helical pitch and the second helical pitch is used for the boundary range. The setting function 75b is one example of a setter.

The display control function 75c displays display data, etc., on the display 72 in accordance with the processing of the processing circuitry 75. For example, the display control function 75c causes the display 72 to display the scan plan set by the setting function 75b. The display control function 75c is one example of a display controller.

The other configurations are the same as the first to third embodiments and the modification.

According to the configurations as discussed, the setting function 75b is provided in the scan planning apparatus 70 that is an external apparatus to the X-ray CT apparatuses 100. With these configurations, the effects and advantages as in the first to third embodiments, etc., are likewise attainable. In addition, the configurations allow for the setting of the scan plan by only providing the processing circuitry 75 of the scan planning apparatus 70 with the setting function 75b, without altering the processing circuitry 34 of the X-ray CT apparatus 100. When there are multiple X-ray CT apparatuses 100 in the X-ray CT system, the setting function 75b need not be provided for each of the X-ray CT apparatuses 100, and therefore, the costs can be reduced.

According to at least one of the embodiments described above, a first imaging range is set within the imaging range for the helical scanning, and at least one of a start range and an end range in the first imaging range is set as a boundary range. Also, a first view number for use in the reconstruction processing for a non-boundary range other than the boundary range in the first imaging range is set, and a view number for use in the reconstruction processing for the boundary range is set to be smaller than the first view number. Accordingly, the X-ray radiations to the areas deviated from the imaging range in the helical scanning can be reduced.

Note that the operations of each component described as a unit member in the above embodiments may be realized by hardware, software, or a combination of hardware and software.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

Additionally, the X-ray CT apparatuses in the embodiments of Japanese Patent Application No. 2017-61289, as a basic application of this application, will be set forth.

[1]: An X-ray CT apparatus according to the embodiments includes a couch top, an X-ray generator, an X-ray detector, a detector, an inputter, a scan controller, and a view-number adjuster. The couch top moves at speeds including at least a first speed and a second speed slower than the first speed, with a subject placed thereon. The X-ray generator generates an X-ray that is emitted to the subject placed on the couch top. The X-ray detector detects the X-ray having passed through the subject, and generates reception data. The detector acquires electrocardiographic waveform data of the subject from an external electrocardiograph. The inputter sets a scan condition for a first scan and a second scan based on an input. In the first scan, the couch top is moved at the first speed in a first imaging range of the subject, for reconstruction with a first view number. In the second scan, the couch top is moved at the second speed in a second imaging range of the subject, for reconstruction with a second view number that is smaller than the first view number and associated with the electrocardiographic waveform data corresponding to a predetermined cardiac phase. The scan controller changes a traveling speed of the couch top and the view numbers based on the scan condition, and controls the X-ray generator for X-ray emission and the X-ray detector for generation of the reception data. The view-number adjuster sets a base point for transition from the first scan to the second scan based on the electrocardiographic waveform data, and sets a view number for use in reconstruction from the first scan in a predetermined transition period before the second scan to be smaller than the first view number.

[2]: The X-ray CT apparatus according to [1], wherein the view-number adjuster decreases the view number to acquire from the first scan in the transition period in a stepwise manner in accordance with the second view number.

[3]: The X-ray CT apparatus according to [1], wherein the view-number adjuster makes the view number to acquire from the first scan in the transition period to be the same as the second view number.

[4]: The X-ray CT apparatus according to [1], wherein the view-number adjuster determines whether or not to adjust the view number to acquire from the first scan in the transition period based on the electrocardiographic waveform data.

[5]: The X-ray CT apparatus according to [4], wherein the view-number adjuster extends the view number to acquire from the first scan in the transition period based on an ON period of the X-ray for the second scan, if the second scan immediately after the transition period coincides with an X-ray ON timing.

What is claimed is:

1. An X-ray CT apparatus adapted to perform helical scanning on a subject placed on a couch top and perform reconstruction processing based on acquired projection data, the X-ray CT apparatus comprising:
    an X-ray generator configured to generate an X-ray for emission to the subject;
    an X-ray detector configured to detect the X-ray via the subject to acquire the projection data; and
    processing circuitry configured to:
        set a first imaging range within an imaging range for the helical scanning, wherein the first imaging range uses a continuous radiation,
        set at least one of a start range and an end range in the first imaging range as a boundary range,
        set a second imaging range adjacent to the boundary range of the first imaging range such that the boundary range is interposed between a non-boundary range of the first imaging range and the second imaging range, wherein the second imaging range uses intermittent radiation,
        set a first view number for use in reconstruction processing for the non-boundary range in the first imaging range,
        set a second view number for use in reconstruction processing for the second imaging range, the second view number being smaller than the first view number and equal to or greater than a half-scan reconstruction mode view number,
        set a third view number for use in reconstruction processing for the boundary range to be smaller than the first view number and equal to or greater than the second view number,
        perform reconstruction processing using the continuous radiation to acquire a first reconstructed image for the non-boundary range using the first view number,
        perform reconstruction processing using the continuous radiation to acquire a second reconstructed image for the boundary range using the third view number,
        perform reconstruction processing, using the intermittent radiation and after completion of the continuous radiation, under a half-scan reconstruction mode to acquire a third reconstructed image for the second imaging range using the second view number,
        set a fourth view number for use in reconstruction processing for the boundary range to be smaller than the third view number and equal to or greater than the second view number, and
        perform reconstruction processing using the continuous radiation to acquire a fourth reconstructed image for the boundary range using the fourth view number.

2. The X-ray CT apparatus according to claim 1, wherein the processing circuitry is configured to set a scan condition so that a first helical pitch is used for the non-boundary range, a second helical pitch narrower than the first helical pitch is used for the second imaging range, and a helical pitch modulated between the first helical pitch and the second helical pitch is used for the boundary range.

3. The X-ray CT apparatus according to claim 1, wherein the processing circuitry is configured to set the third view number for use in the reconstruction processing for the boundary range to decrease in a stepwise manner.

4. The X-ray CT apparatus according to claim 1, wherein the processing circuitry is configured to set the fourth view number for use in the reconstruction processing for the boundary range and the second view number to be an equal value.

5. The X-ray CT apparatus according to claim 1, wherein the processing circuitry is configured to acquire electrocardiographic waveform data of the subject from an external electrocardiograph, and determine whether or not the fourth view number for use in the reconstruction processing for the boundary range should be adjusted based on the electrocardiographic waveform data.

6. The X-ray CT apparatus according to claim 5, wherein the processing circuitry is configured to extend the fourth view number for use in the reconstruction processing for the boundary range based on a period to generate the X-rays after the boundary range, if the second imaging range after the boundary range coincides with an X-ray generation timing.

7. A scan planning apparatus adapted to set a scan plan for an X-ray CT apparatus which performs helical scanning on a subject placed on a couch top and performs reconstruction processing based on acquired projection data, the scan planning apparatus comprising:
  processing circuitry configured to set the scan plan by:
    setting a first imaging range within an imaging range for the helical scanning, wherein the first imaging range uses a continuous radiation,
    setting at least one of a start range and an end range in the first imaging range as a boundary range,
    setting a second imaging range adjacent to the boundary range of the first imaging range such that the boundary range is interposed between a non-boundary range of the first imaging range and the second imaging range, wherein the second imaging range uses intermittent radiation,
    setting a first view number for use in reconstruction processing for the non-boundary range in the first imaging range,
    setting a second view number for use in reconstruction processing for the second imaging range under a half-scan reconstruction mode, the second view number being smaller than the first view number and equal to or greater than a half-scan reconstruction mode view number,
    setting a third view number for use in reconstruction processing for the boundary range to be smaller than the first view number and equal to or greater than the second view number, and
    setting a fourth view number for use in reconstruction processing for the boundary range to be smaller than the third view number and equal to or greater than the second view number; and
  communication circuitry configured to send the set scan plan including the fourth view number to the X-ray CT apparatus.

8. The scan planning apparatus according to claim 7, wherein the processing circuitry is configured to set the scan plan so that a first helical pitch is used for the non-boundary range, a second helical pitch narrower than the first helical pitch is used for the second imaging range, and a helical pitch modulated between the first helical pitch and the second helical pitch is used for the boundary range.

* * * * *